(12) United States Patent
Dimitriadis et al.

(10) Patent No.: US 10,481,095 B2
(45) Date of Patent: Nov. 19, 2019

(54) METHODS AND MEANS FOR MULTISPECTRAL IMAGING

(71) Applicant: Universität Heidelberg, Heidelberg (DE)

(72) Inventors: Nikolas Dimitriadis, Mannheim (DE); Nikolaos Deliolanis, Stuttgart (DE)

(73) Assignee: Universität Heidelberg, Heidelberg (DE)

( * ) Notice: Subject to any disclaimer, the term of this patent is extended or adjusted under 35 U.S.C. 154(b) by 0 days.

(21) Appl. No.: 15/316,455

(22) PCT Filed: Jun. 3, 2015

(86) PCT No.: PCT/EP2015/062447
§ 371 (c)(1),
(2) Date: Dec. 5, 2016

(87) PCT Pub. No.: WO2015/185661
PCT Pub. Date: Dec. 10, 2015

(65) Prior Publication Data
US 2017/0167980 A1 Jun. 15, 2017

(30) Foreign Application Priority Data

Jun. 5, 2014 (EP) .................................... 14171378
Mar. 24, 2015 (EP) .................................... 15160630

(51) Int. Cl.
*G01N 21/64* (2006.01)
*G01N 21/91* (2006.01)
(Continued)

(52) U.S. Cl.
CPC ......... *G01N 21/6456* (2013.01); *A61B 1/043* (2013.01); *A61B 1/0638* (2013.01);
(Continued)

(58) Field of Classification Search
CPC ........... G01N 21/6428; G01N 21/6456; G01N 21/718; G01N 21/80; G01N 21/91;
(Continued)

(56) References Cited

U.S. PATENT DOCUMENTS 6,110,106 A * 8/2000 MacKinnon ......... A61B 5/0071
600/160
6,760,105 B2 * 7/2004 Oshida ............... G01N 21/6428
250/458.1

(Continued)

FOREIGN PATENT DOCUMENTS

CN 1289239 3/2001
CN 101528116 A 9/2009
(Continued)

OTHER PUBLICATIONS

International Search Report issued in PCT/EP2015/062447; dated Sep. 21, 2015.

(Continued)

*Primary Examiner* — Taeho Jo
(74) *Attorney, Agent, or Firm* — Studebaker & Brackett PC

(57) ABSTRACT

Multispectral imaging of samples, in particular of biological tissues. A method for acquisition of fluorescence and reflectance images of an object including alternatingly illuminating the object with at least a first light having several spectral regions of high intensity, wherein the first light has at least one region of low intensity that is of longer wavelength to a region of high intensity, and at least a second light having at least one spectral region of high intensity, recording a first image of the object during illumination of the object with the first light and a second image of the object during illumination of the object with the second light using a common sensor array, wherein the light recorded by the sensor array (Continued)

Figure 1:
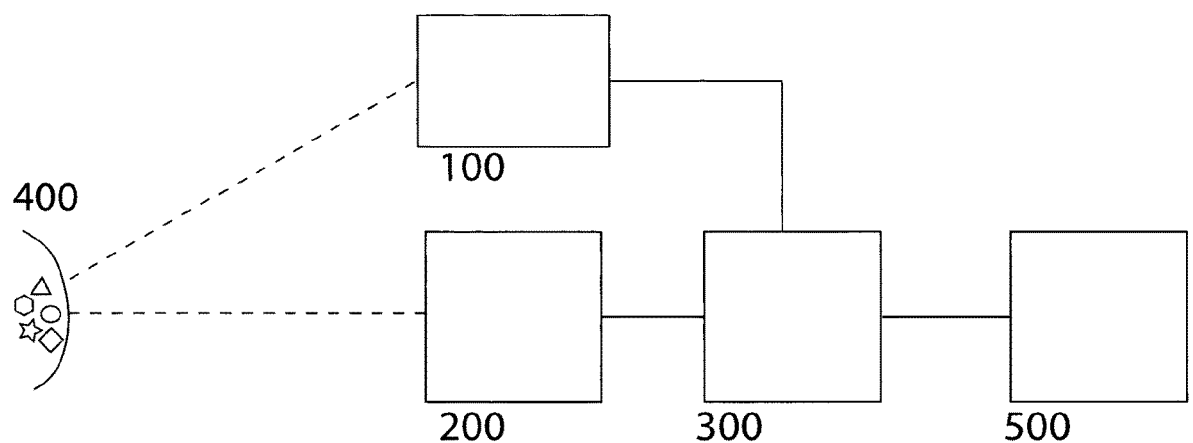

is attenuated in at least one of the spectral regions in which the first light has high intensities.

17 Claims, 37 Drawing Sheets

(51) Int. Cl.
| | |
|---|---|
| G01J 3/44 | (2006.01) |
| A61B 1/04 | (2006.01) |
| A61B 1/06 | (2006.01) |
| A61B 5/00 | (2006.01) |
| G01J 3/10 | (2006.01) |
| G01N 21/80 | (2006.01) |
| A61B 5/1455 | (2006.01) |
| A61B 3/14 | (2006.01) |

(52) U.S. Cl.
CPC .............. A61B 3/14 (2013.01); A61B 5/0071 (2013.01); A61B 5/14551 (2013.01); G01J 3/10 (2013.01); G01J 3/4406 (2013.01); G01N 21/6428 (2013.01); G01N 21/80 (2013.01); G01N 21/91 (2013.01); G01J 2003/102 (2013.01); G01J 2003/106 (2013.01); G01N 2021/6439 (2013.01)

(58) Field of Classification Search
CPC ..... G01N 27/44721; G01N 2021/6417; G01N 2021/6439; A61B 5/0059; A61B 1/043; A61B 1/0638; A61B 5/0071; A61B 3/14; A61B 5/14551; G01J 3/4406; G01J 3/10; G01J 3/32; G01J 2003/102; G01J 2003/106
USPC ........................................................ 250/459.1
See application file for complete search history.

(56) References Cited

U.S. PATENT DOCUMENTS

| | | | |
|---|---|---|---|
| 7,904,139 B2* | 3/2011 | Chance | A61B 5/0059 600/407 |
| 8,849,380 B2* | 9/2014 | Patwardhan | A61B 5/0059 600/476 |
| 2002/0140933 A1* | 10/2002 | Oshida | G01N 21/6428 356/317 |
| 2003/0191368 A1* | 10/2003 | Wang | A61B 1/00009 600/160 |
| 2004/0184648 A1* | 9/2004 | Zhang | G06T 7/586 382/141 |
| 2006/0232776 A1* | 10/2006 | Hairston | G01J 3/02 356/388 |
| 2007/0170063 A1* | 7/2007 | Yamazaki | G01N 27/44721 204/601 |
| 2008/0062429 A1* | 3/2008 | Liang | A61B 1/00039 356/497 |
| 2009/0040754 A1* | 2/2009 | Brukilacchio | A61B 1/0653 362/228 |
| 2009/0042179 A1* | 2/2009 | Peltie | A61B 1/0638 435/4 |
| 2009/0137908 A1* | 5/2009 | Patwardhan | A61B 5/0059 600/476 |
| 2009/0323058 A1* | 12/2009 | Dyba | G01N 21/65 356/301 |
| 2010/0016669 A1* | 1/2010 | Takaoka | A61B 1/043 600/160 |
| 2010/0157039 A1* | 6/2010 | Sugai | A61B 1/00009 348/68 |
| 2010/0168586 A1* | 7/2010 | Hillman | G02B 23/2476 600/476 |
| 2010/0296141 A1* | 11/2010 | Maruyama | H04N 1/02865 358/509 |
| 2011/0230738 A1* | 9/2011 | Chance | A61B 5/0059 600/310 |
| 2012/0013722 A1* | 1/2012 | Wong | A61B 1/00009 348/66 |
| 2012/0016230 A1 | 1/2012 | Kishima et al. | |
| 2012/0085932 A1 | 4/2012 | Themelis | |
| 2012/0099190 A1* | 4/2012 | Knebel | G02B 21/002 359/385 |
| 2013/0012794 A1* | 1/2013 | Zeng | A61B 1/00186 600/328 |
| 2013/0114078 A1* | 5/2013 | Honda | G01N 21/9501 356/364 |
| 2013/0191368 A1 | 7/2013 | Raichelgauz et al. | |
| 2013/0286176 A1 | 10/2013 | Westwick et al. | |
| 2013/0296710 A1* | 11/2013 | Zuzak | A61B 5/0071 600/476 |
| 2013/0302746 A1* | 11/2013 | Liang | A61B 1/0638 433/29 |
| 2013/0329006 A1* | 12/2013 | Boles | H04N 1/40056 348/42 |
| 2014/0187967 A1* | 7/2014 | Wood | A61B 5/0071 600/473 |
| 2014/0218726 A1* | 8/2014 | Cheng | G01N 21/65 356/301 |
| 2014/0293091 A1* | 10/2014 | Rhoads | G01J 3/513 348/234 |
| 2015/0051497 A1* | 2/2015 | Carver | A61B 5/0071 600/476 |
| 2015/0087902 A1* | 3/2015 | Mertz | G02B 21/14 600/109 |
| 2015/0092035 A1* | 4/2015 | Yamamoto | G02B 21/06 348/68 |
| 2017/0209050 A1* | 7/2017 | Fengler | G02B 21/16 |

FOREIGN PATENT DOCUMENTS

| | | |
|---|---|---|
| CN | 101583934 | 11/2009 |
| CN | 103262522 A | 8/2013 |
| JP | 2002-287034 A | 10/2002 |
| JP | 2006-525494 A | 11/2006 |
| JP | 2009-012203 A | 1/2009 |
| WO | 2009/021079 A1 | 2/2009 |

OTHER PUBLICATIONS

Written Opinion issued in PCT/EP2015/062447; dated Sep. 21, 2015.
Japanese Office Action dated Feb. 27, 2018 issued in corresponding Japanese Patent Application No. 2016-571099 with English translation; 12pp.
Chinese Office Action dated Feb. 2, 2018 issued in corresponding Chinese Patent Application No. 201580042447.8 with English translation; 18pp.
Japanese Office Action dated Feb. 5, 2019 issued in corresponding Japanese Patent Application No. 2016-571099 with English translation; 11pp.

* cited by examiner

LED4

LED3

Fig. 24

Bayer
RGGB

RGIRB      CMYG      ABCDEFGHI time and spectral multiplexing timing of the shutter and ambient illumination

METHODS AND MEANS FOR MULTISPECTRAL IMAGING

The present invention relates to the multispectral imaging of samples, in particular of biological tissues.

When imaging tissue the illumination light may be absorbed or scattered. If the tissue contains fluorescence molecules, then the absorbed energy is temporarily stored by setting the molecules at an excited state and then it is partially released as a photon of longer wavelength. The intensity of the light emitted as fluorescence is usually many orders of magnitude weaker than the intensity of the excitation light that has been reflected and, thus, it is necessary to separate or block the reflected light from the emitted light.

The most practical way is using band-pass filters in the excitation and the emission paths of the beams to limit the spectral range of the lights to avoid bleed-through of reflected excitation in the recorded emission path. A direct consequence of this method is that it is not possible to acquire the fluorescence image simultaneously with the reflected excitation image in the same detection path.

In order to acquire both the fluorescence and the reflected images it is necessary to switch between the two modes of acquisition: with and without filters. For a static object, i.e. for an object that doesn't move significantly during the acquisition of the fluorescence and reflectance images, it is never a problem to switch between filters and acquire the two images sequentially. However, if the objects in the field of view move, then the recorded images are not coinciding, and registration can be very difficult even after intensive image processing.

Yet, another problem that can arise is the simultaneous imaging of multiple fluorescent agents that have different excitation and emission characteristics. In this case, different sets of imaging filters for excitation and emission must be used to image the different fluorochromes, which eventually increases the complexity and the number of acquired images. Moreover, when imaging moving objects it is necessary to record both the emitted fluorescence and the reflected excitation of an object with rather high video frame rates. Switching between filters must then be accomplished very fast.

There are several approaches that are used to achieve multispectral imaging. They can be roughly characterized by a) the number of sensors used, b) the use of switching filters, c) switching between different illuminations or, d) the use of multiple band pass filters, the use of beam splitters, etc. [Y. Garini, I. T. Young, and G. McNamara, "Spectral imaging: Principles and applications," Cytometry Part A 69A, 735-747 (2006)]

These prior art techniques will be described in detail in the following.

[Switching Filters]

Some multispectral imaging systems have a single image sensor and implement a fast switching mechanism between reflectance and fluorescence imaging mode. This can be achieved with use of bandpass excitation and emission filter sets that are mounted on filter wheels or filter cubes that are exchanged fast in order to record reflectance and fluorescence images alternatingly with high frequency. This approach is straightforward and allows the highest throughput of light, but requires mechanically moving parts like filter wheels. Further, depending on the filter configuration, it allows the recording of the intensity of only one fluorophore at a time. Switching filters at near video rate frequencies is technically complex and requires accurate mechanical synchronization with the frame grabbing sequence of the camera.

To avoid mechanical components one may use spectrally tunable filters, for example liquid crystal tunable filters. The switching between spectral settings suitable for different fluorophores can be very fast (<1 ms), however the transmission throughput of the tunable filters is limited. Furthermore, they are highly sensitive to light transmission angles and light polarization, and are associated with rather high costs.

[Beam Splitters]

An alternative approach for multispectral imaging is to use multiple sensors, where in front of each sensor a corresponding emission filter is arranged. The light can reach each sensor either by passing through a single objective lens and using an optical beam-splitter arrangement to deliver the light to each sensor, or each sensor can have a separate objective lens. In any case, each sensor is paired with a filter that can block the excitation wavelengths and record the emission from one fluorophore [Lucia M. A. Crane et al., et al. J Vis Exp. 2010; (44): 2225.]. An additional sensor can record the reflection image with a different imaging path. This concept is simple, but the use of multiple sensors, beam splitters or objective lenses increases the size, the complexity of design and the cost.

[Fast Switching Illumination]

Another solution for multispectral imaging uses switching between different excitation lights. Therein, the object is alternatively illuminated with excitation beams that have a specific excitation spectrum that is blocked by filters to enter into one or more cameras. In US 20130286176 A1 a single color sensor, a laser excitation to excite fluorescence, and a broadband illumination source that switches on and off, is used. When only the laser excitation source is on, then the sensor can capture the emitted fluorescence, and when the broadband illumination is on, then the sensor can capture the reflected image. This system produces a reflectance image and an image of a fluorochrome, but an observer might visually experience a disturbing flickering due to the on-off switching of the different sources.

[Blocking Multiple Bandpass Images]

Yet another approach uses filters with multiple-band pass regions paired with a monochrome sensor. In this approach a filter in front of a monochrome sensor blocks the excitation wavelengths to enter into the monochrome sensor. The different fluorophores can be imaged individually with excitation scanning. Alternatively the filtered multi-component fluorescent light can be split into wavelength dependent paths which are then imaged onto different spatial regions of a monochrome sensor. With this approach it is possible to record multiple channels simultaneously with a monochrome sensor.

In an alternative approach a color sensors can be used to record the multi-component fluorescent light with a multi-channel (and thus color) sensor. The multi-channel sensor output can then be processed in order to obtain the individual fluorescent components.

An additional sensor can be used to record the reflectance image by splitting the reflected excitation light into a different optical path imaging that light on that sensor. This offers multiple fluorescence imaging bands together with the reflectance, but an observer will visually perceive false color representation. Depending on the specific excitation wavelengths, the false perception might not be possible to be corrected even digitally.

It is possible to further split both, the reflectance and the fluorescence onto multiple additional color sensors to increase the number of spectral channels. Each channel has a narrow bandpass filter in front of the sensor and the intensity in each individual narrow filter band is computed [US 20120085932 A1].

The used filter sets are known as "Pinkel", "Sedat", or "Full-multiband" depending on the exact combination of excitation and emission filters used in the specific application.

The present invention is made to provide a method and means for multispectral imaging, which avoid the above mentioned problems of the prior art and are simple, quick and cost effective.

This problem is solved by the method according to claim 1 and the apparatus according to claim 9 as well as the endoscope or surgical microscope according to claim 15 and their uses according to claim 16. Advantageous improvements are provided in the respective dependent claims.

According to the present invention a method for acquisitions of fluorescence and reflectance images of an object is provided. In this inventive method an object is alternatingly illuminated with two different lights. These at least two different lights comprise at least one first light and one second light, which are alternatingly directed onto the object. The first light has several spectral regions of high intensity and at least one region of low intensity, that is of longer wavelength to a region of high intensity, while the at least second light has at least one spectral region of high intensity.

During alternatingly illuminating the object with these two lights, a common sensor array records images. During illumination of the object with the first light and the second light separate images of the illuminated object are recorded. Further the recorded light, i. e. the light emitted by the object and directed onto the common sensor array in at least one of the spectral regions, in which the first light has high intensity, is attenuated.

By alternatingly illuminating the object with said first light and said second light it is thus possible to record during illumination with the first light a fluorescence image of the object. During illumination with the second light it is possible to record a reflectance image of the object.

In a first advantageous improvement, the sensor array, which is common to record the fluorescence image and the reflectance image alternatingly, is a multichannel array, preferably a color sensor array. Such a multichannel array records the images in the channel image space, for example in the color image space of a color sensor. These image data are then transformed into values of a component image space, where the components space preferably corresponds to the spatial distributions of fluorochromes, absorbers, derived values thereof or noise. Thus in the present invention first images are recorded in the channel image space, for example in the color images space, and then transferred to an image, which displays e. g. lateral distribution of specific fluorochromes, absorbers, etc.

As mentioned before, the first light and/or the second light may have spectral regions of high intensity and spectral regions of low intensity. In order to record the above mentioned fluorescence images and reflectance images, it is of advantage, if the light intensity ratio between a region of high intensity at shorter wavelength and a neighboring region of low intensity at longer wavelength, is at least $1*10^2$, preferably $\geq 1*10^6$.

Further, as mentioned above, the light recorded by the sensor array is attenuated in at least one of the spectral regions in which the first light has high intensities. The attenuation ratio between the intensity of the unattenuated and the attenuated spectral region preferably is at least $1*10^2$, preferably at least $1*10^3$, preferably at least $1*10^6$. In an alternative embodiment, the amount of attenuation of the light recorded by the sensor array in at least one of the spectral regions in which the first light has high intensity is such that the intensity of the light recorded in unattenuated spectral regions is preferably higher than the intensity of the light recorded in the sum of the attenuated second spectral regions.

In particular, the light recorded by the sensor array may be filtered by a multiple bandpass filter.

In a preferable arrangement of the present invention the first light and/or the second light are generated by broadband light, which is then filtered by the respective multiple bandpass filters to generate the first light and the second light. To achieve that, said multiple bandpass filters for the first light and the second light can have complimentary filter regions, such that ranges of high light intensity of the first light alternate with ranges of high light intensity of the second light.

A similar light distribution for the first light and the second light can be achieved by using multiple narrowband light sources for the first light and the second light, where the emission peaks of the light sources used for the first light and the emission peaks of the light sources for the second light are alternating along the spectral wavelength axis.

Also combinations of the above-mentioned concepts to generate the first light and the second light are possible.

By such an arrangement, it is possible to record alternatingly fluorescence images and reflectance images in the same spectral regions transmitted by the multiple bandpass filter in front of the common sensor array. In a preferable scenario, the wavelengths regions, which are excluded from recording by said multiple bandpass filter in front of the common sensor array may not be critical for the visualization of the reflection image, as the recorded spectral parts can be used to reconstruct a color image.

As a higher number of components (i.e. fluorophores) is imaged, separate images may be recorded by using a higher number of different first lights. The number of components (fluorochromes) that can be unmixed depends mainly on the number of color channels. Using e.g. an RGB sensor, up to 3 fluorochromes can be unmixed. E.g. using one additional first light with the same RGB sensor, up to 6 fluorochromes can be unmixed. Said first lights should preferably be adapted to the excitation spectrum of said fluorophores, whereas the recorded light needs to be selected according to the emission spectrum of all the fluorophore of interest. For measuring fluorescence images, it might be necessary to keep the surrounding of the imaging apparatus dark during image recording, in order to reduce the non-fluorescent light. However, in particular in medical applications, it might be necessary to provide additionally ambient light in order for the operating person to view the environment. For this purpose, it is suggested to alternatingly illuminate the object with at least one first light and at least one second light and further in a further time period with pulses of a further light, wherein the pulse duration of the further light is short compared to the illumination periods used for illuminating the object with the at least first light and the at least second light. Said further light may also be applied during application of either the at least first light or the second light, while recording of the first image and the second image is halted during illumination with said further light. Preferably the light pulses of the further light are correspondingly short compared to the duration of the first or second light.

Said further light may then be sufficiently strong in order to provide the persons working in the surrounding of the inventive imaging apparatus with sufficient light for observing this surrounding. If the frequency of said further light parts is high enough, the persons working in the surrounding may be provided with a continuous visual effect.

In the following different examples of the present invention are provided. Therein for similar or same elements similar or same reference numbers are used. In the following examples a combination of features which are essential and optional for the present invention may be described in combination. However, each of the optional features described in such a combination may be used, to separately and singly improve the invention as described in the present claims.

The examples are shown in combination with

FIGS. 1 to 35, which all show aspects of inventive examples.

EXAMPLE 1

FIG. 1 describes the general concept of the invention. The inventive system comprises an illumination system 100 that produces and guides light that incorporates spectral and time multiplexing properties to illuminate an object 400. The light emanating from the object 400 is collected and detected or imaged by an imaging system 200 that is comprised of elements like lenses, filters, and a light sensor/detector array (i.e. camera), etc. Both the illumination system 100 and the detection system 200 are connected to a controlling and processing unit (300) that controls the operation of the illumination system 100, synchronizes the operation and grabs the images from the detecting system 200, and processes the image data, for further evaluation, display and storage. Finally, a display/visualization system 500 displays the decomposed images either separately or simultaneously/in overlay.

Figure 2:
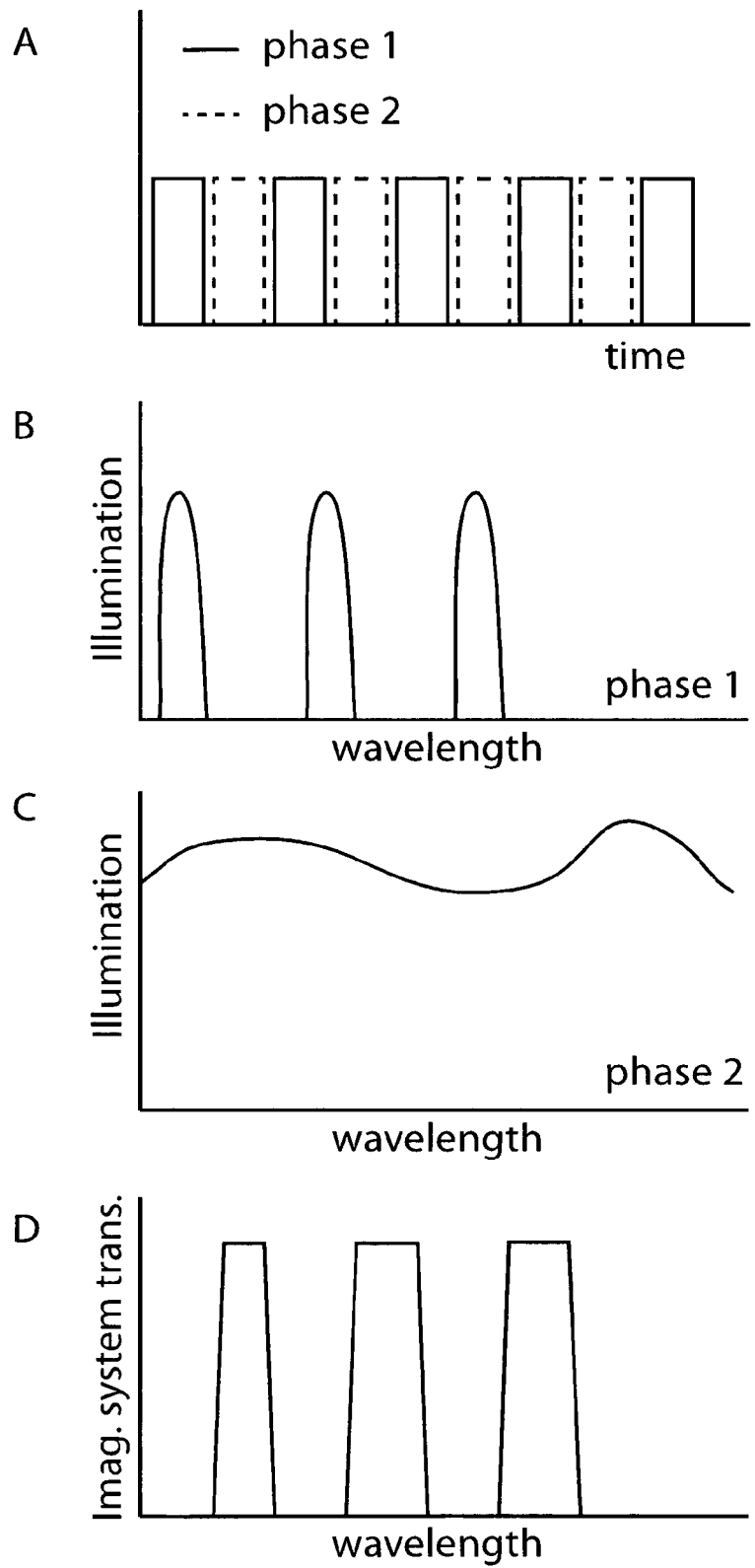

The illumination system 100 operates in two (or more) alternating phases as shown in FIG. 2. FIG. 2A shows the time course of different phases, FIG. 2B the spectrum of the first light, FIG. 2C the spectrum of the second light and FIG. 2D the transmission of incident light to be detected.

In phase 1, the system illuminates the object with light exhibiting a spectral shape with areas of high and low intensities as depicted in FIG. 2B. Various spectral shapes are possible, but it is essential that the light has spectral regions with very low intensity at wavelengths longer than the high intensity regions. In those regions fluorescent light emitted by the object upon excitation with the first light can be detected by the imaging system without detecting relevant amounts of reflected light. In phase 2 the object is illuminated with a broadband light as shown in FIG. 2C.

The imaging system 200 comprises one imaging channel/path. The imaging channel has an image sensor array setup to detect and record fluorescence and reflectance images at the different phases. The light reaching the image sensor is spectrally attenuated so that in general the illumination light of phase 1 is attenuated before reaching the imaging sensor as shown by the transmission spectrum of the attenuator in FIG. 2D.

By alternating the illumination of the object it is possible to alternatively record complementary reflectance and fluorescence images with the same sensor in the same spectral regions. In illumination phase 1 the spectral bands of the light reflected from the object are attenuated and essentially only the fluorescence emission is transmitted and detected by the sensor array forming a fluorescence image, whereas in phase 2 the reflected light from the object is partially transmitted and recorded with the sensor to form a reflectance image.

The amount of attenuation of the spectral regions to be attenuated before the light reaches the sensor can be approximately estimated such that when the sensor is preferably used to detect fluorescence the detected fluorescence signal should preferably be more than the bleed-through of the excitation light.

EXAMPLE 2

Figure 3:
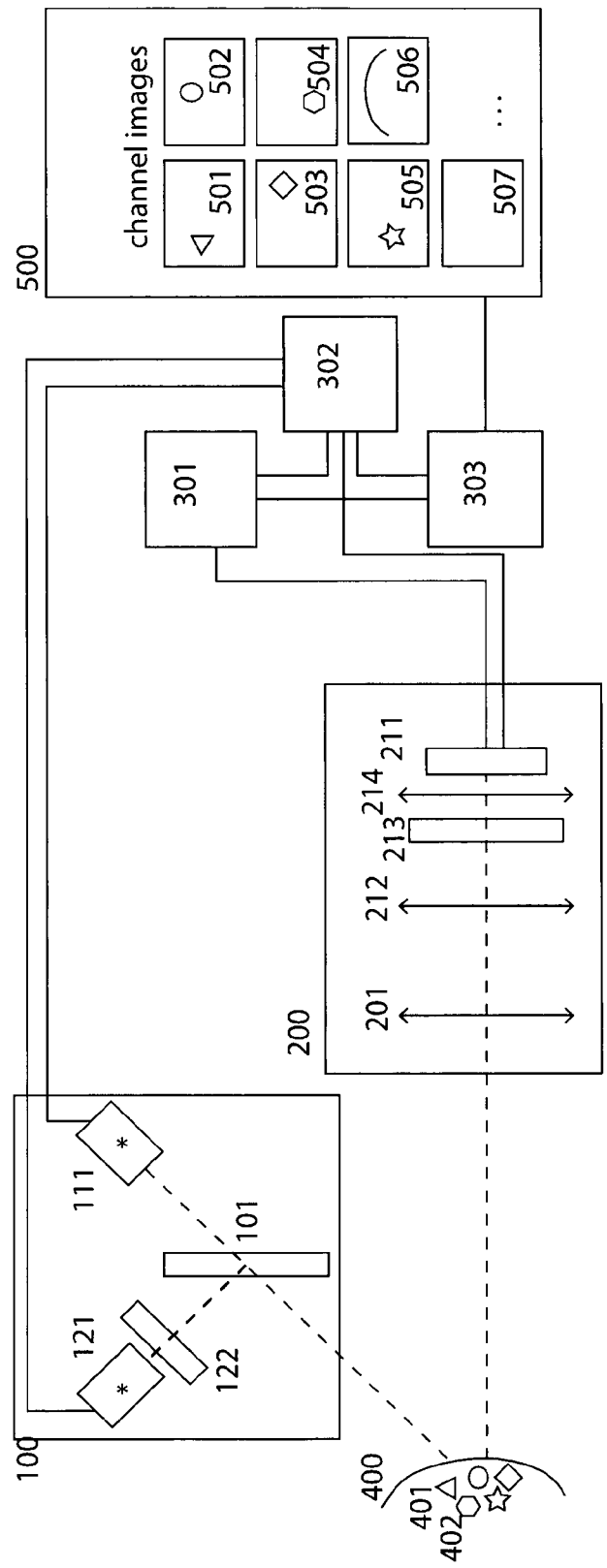

One of the preferred embodiments is shown in FIG. 3. Therein two broadband white light sources (111 and 121) are used, which can be switched on and off alternatively. One is filtered with a multiple bandpass filter 122. The two beams from these two sources 111 and 121 are combined by a multiple bandpass polychroic mirror 101. In between those elements, collimation lenses may optionally be placed in order to guide more light to the area to be imaged. The light emitted by the object 400 is collected in the detection system 200 with an objective lens 201 (or a system of lenses acting as an objective lens), which for use in open surgeries preferably has a focusing distance of 200 mm. A multiple bandpass filter 213 that is complementary to the filter 122 attenuates the beam. The filtered beam is then imaged by a multichannel or multi-color sensor array 211. The processing/controlling unit 300 is consisted by a frame grabber 301, a controlling unit 302 and a processing unit 303 to generate images 501, ... , 507 ... . Optional lenses 212, 214 can be used in between the various elements to relay the image to the sensor. The multi-bandpass filter 213 is preferably placed in an optically infinity corrected imaging space.

Figure 4:
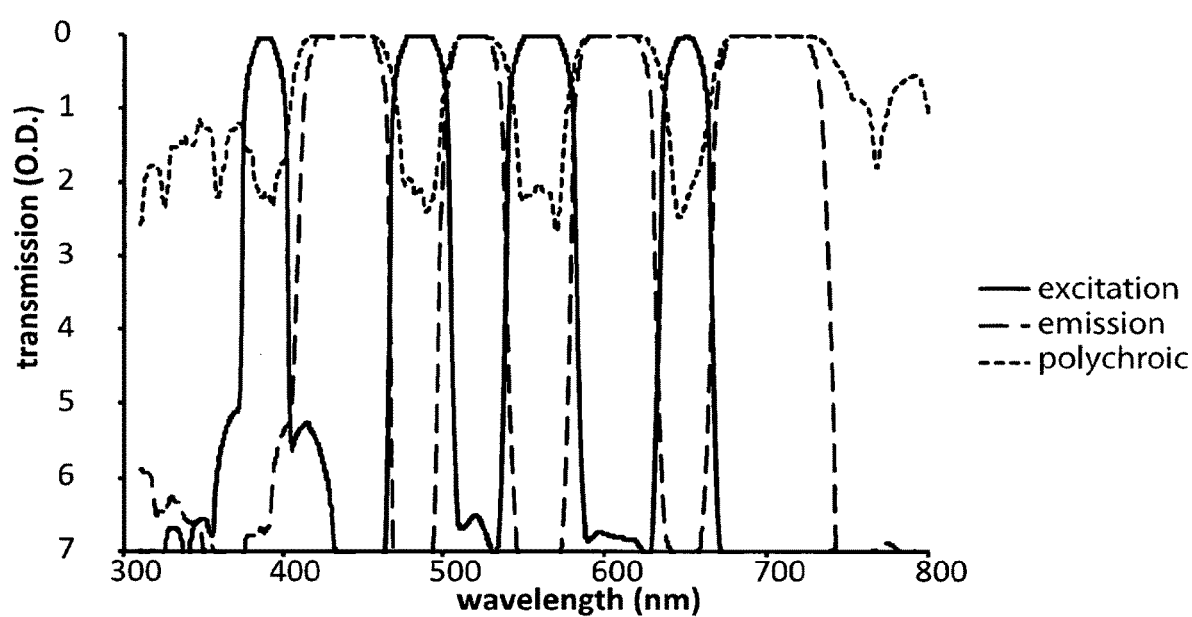

The multiple bandpass filters and the polychroic filter are usually manufactured as excitation/emission/mirror filter sets for use in fluorescence microscopy as Sedat, Pinkel or full multiband sets. An example for transmission spectra of a four-band filter set which is originally configured for imaging four fluorochromes is shown in FIG. 4. The "excitation filter" is used in position 122, the "polychroic mirror" in 101, and the "emitter filter" in position 213. Various different combinations of filters and various filter sets may be used for various fluorochrome applications. Usually there is a small gap between the filter transmission bands to avoid crosstalk (see schematics). The width of that band depends on the characteristics of the filter to operate under a range of angles of incidence combined with the requirement of the filter set to perform in an environment with realistic conditions.

Using such a filter set for the two illumination modes means that in phase 1 the excitation filter of the set is used to filter white light originating from source 111, the polychroic mirror is used as element 101 to combine the beams from sources 111 and 121 in one, and the emission filter is used as filter 213 in 122 to block the excitation light from 111. In practical terms and assuming nominal concentrations of fluorochromes in tissue (usually between $100 \times 10^{-9}$ M to $1 \times 10^{-3}$ M with 1 M=1 mol/liter) the usual attenuation ratio in the rejection bands of interference multiple bandpass filters of optical density (O.D.) of 6 orders of magnitude is sufficient, however it is expected that in many cases attenuation of 2 or 3 O.D. can be adequate.

Figure 5:
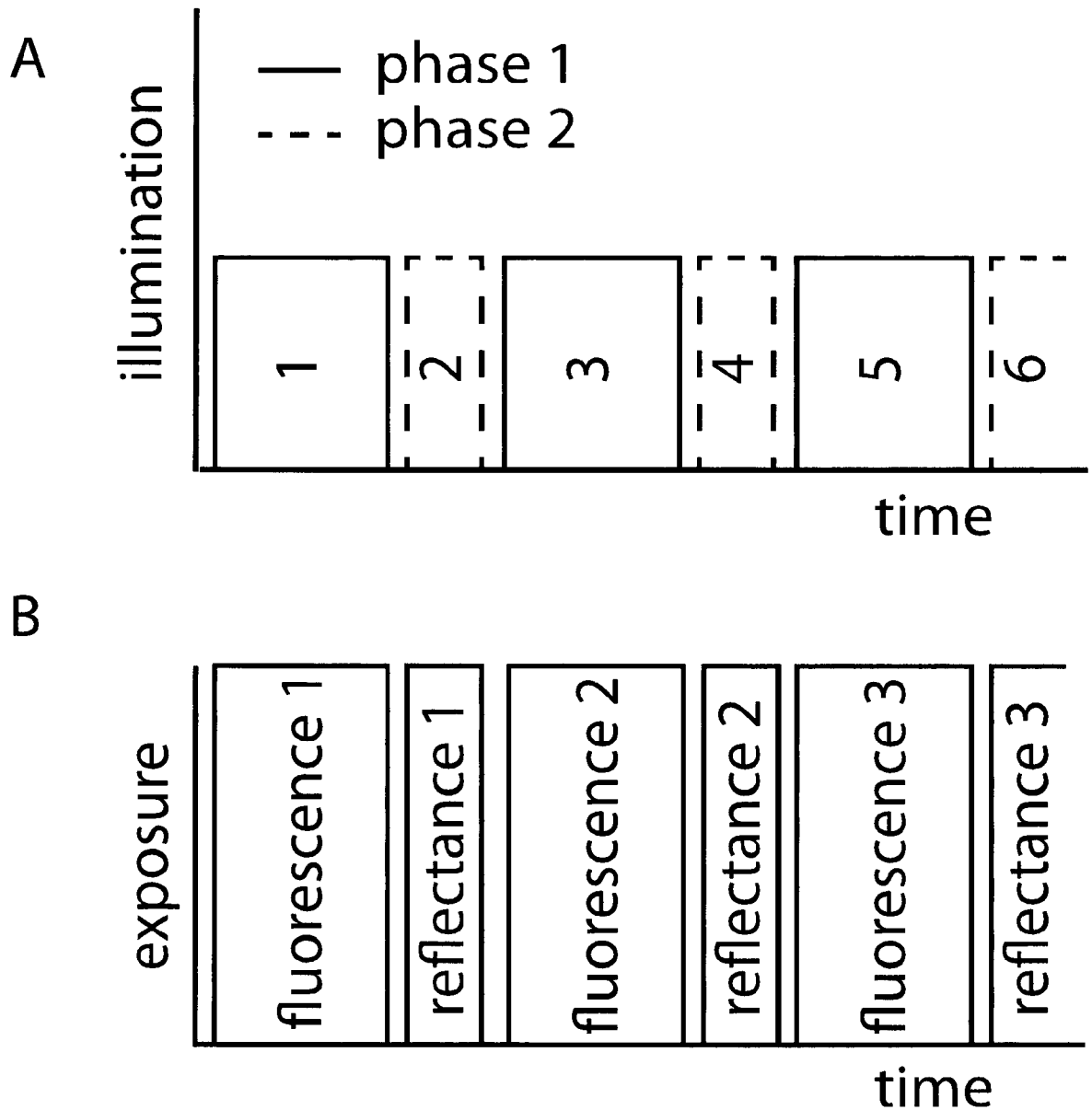

In phase 1, the object 400 is illuminated with spectrally shaped light from source 111 that is at least partially reflected, transmitted, and absorbed by the object 400 to excite fluorescence. The excitation light reflected by object 400 in phase 1 is attenuated by the emission filter 213 in front of sensor 211, which thus records only fluorescence emission. In phase 2 the object 400 is illuminated with broadband light from source 121. This light is partially reflected by the object 400, which emits reflected light and fluorescence. The filter 213 transmits only some bands of the reflected and fluorescence emitted light. Since the fluorescence light intensity is usually many orders of magnitude lower than the reflected light, it can be assumed that practically only a reflectance image is recorded. To summarize, in phase 1 the sensor 211 records fluorescence and in phase 2 records the reflectance image of the object in the spectral regions where filter 213 shows sufficient transmission. Usually the fluorescence image has a much lower intensity than the reflectance image. In order to accommodate for the different dynamic ranges a longer exposure time should be used for the fluorescence image. Such a sequence of the phases and the images is shown in FIG. 5. Here, FIG. 5A shows the timely sequence of illumination phases 1 and 2, where phase 1 is longer than phase 2. FIG. 5B shows the timely sequence of detection phases 1 and 2 where the phases 1 for detection of fluorescence images are longer than phases 2 for detection of reflectance images.

The controlling of the illumination of the object and the exposure of the sensor is provided from signals in the processing and controlling unit 300. The two broadband light sources 111 and 121 can be incandescent lamps, gas lamps (like Hg, Xe, or mixtures), light emitting diodes (LEDs), or any other broadband light source. LED sources can be switched on and off at a high frequency rate, with rise and fall times faster than 100 microseconds. Such a system can illuminate the object with alternating phases at video rate, i.e. approximately at 25 fps (frames per second). At this and at higher illumination rates the visual perception of the illumination field is uniform, where any flickering effect is hardly observable.

Figure 6:
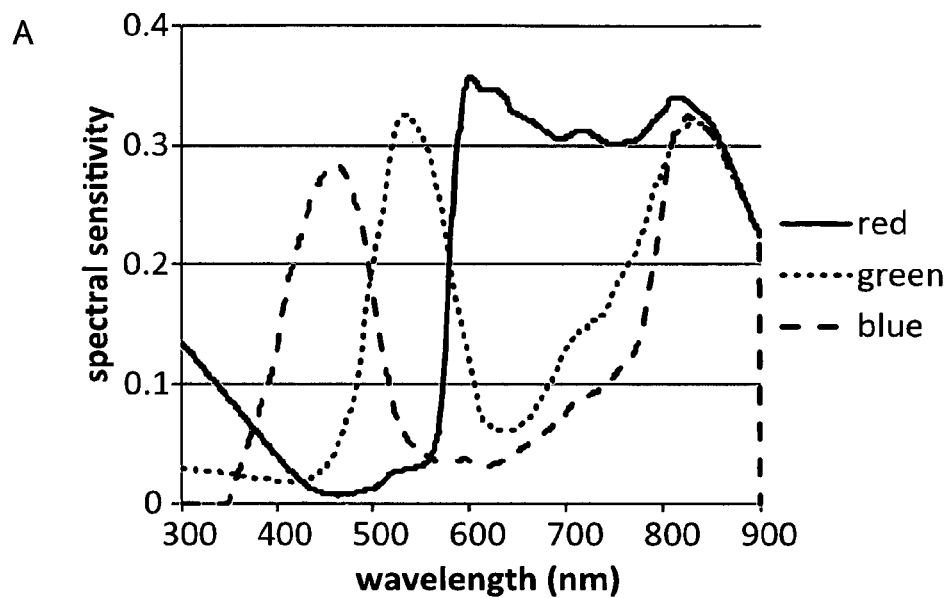
Figure 6:
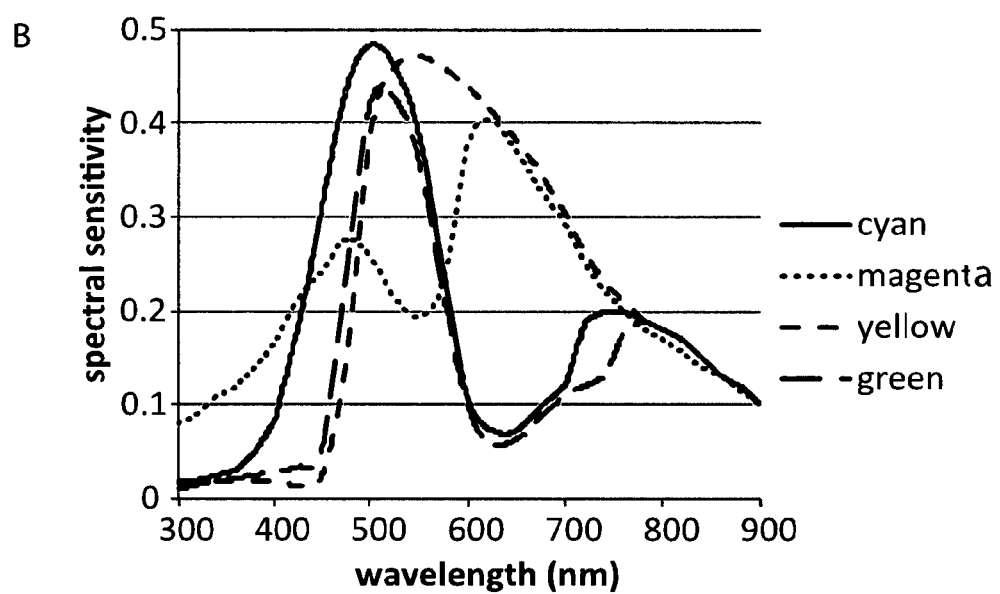

The sensor 213 is preferably a multichannel (multi color) sensor that has the capability to record the images with multiple channels. Each spectral area has a distinct spectral sensitivity and records the reflected light of a spectral multiplex of various reflecting and fluorescence substances in the object. Examples of a multichannel color sensors arrays are the RGB (red-green-blue) or the CMYG (cyan-magenta-yellow-green) pattern sensors. Typical color sensitivities of different types of color sensors are shown in FIG. 6. In FIG. 6A, sensitivities of red, green and blue sensor elements of an RGB sensor are shown. In FIG. 6B sensitivities of cyan, magenta, yellow and green sensor elements of a CMYG sensor are shown. Thus, the data recorded by these sensors are data in a respective color space, i.e. a space spanned by the respective colors, e. g. RGB or CMYG.

Figure 7:
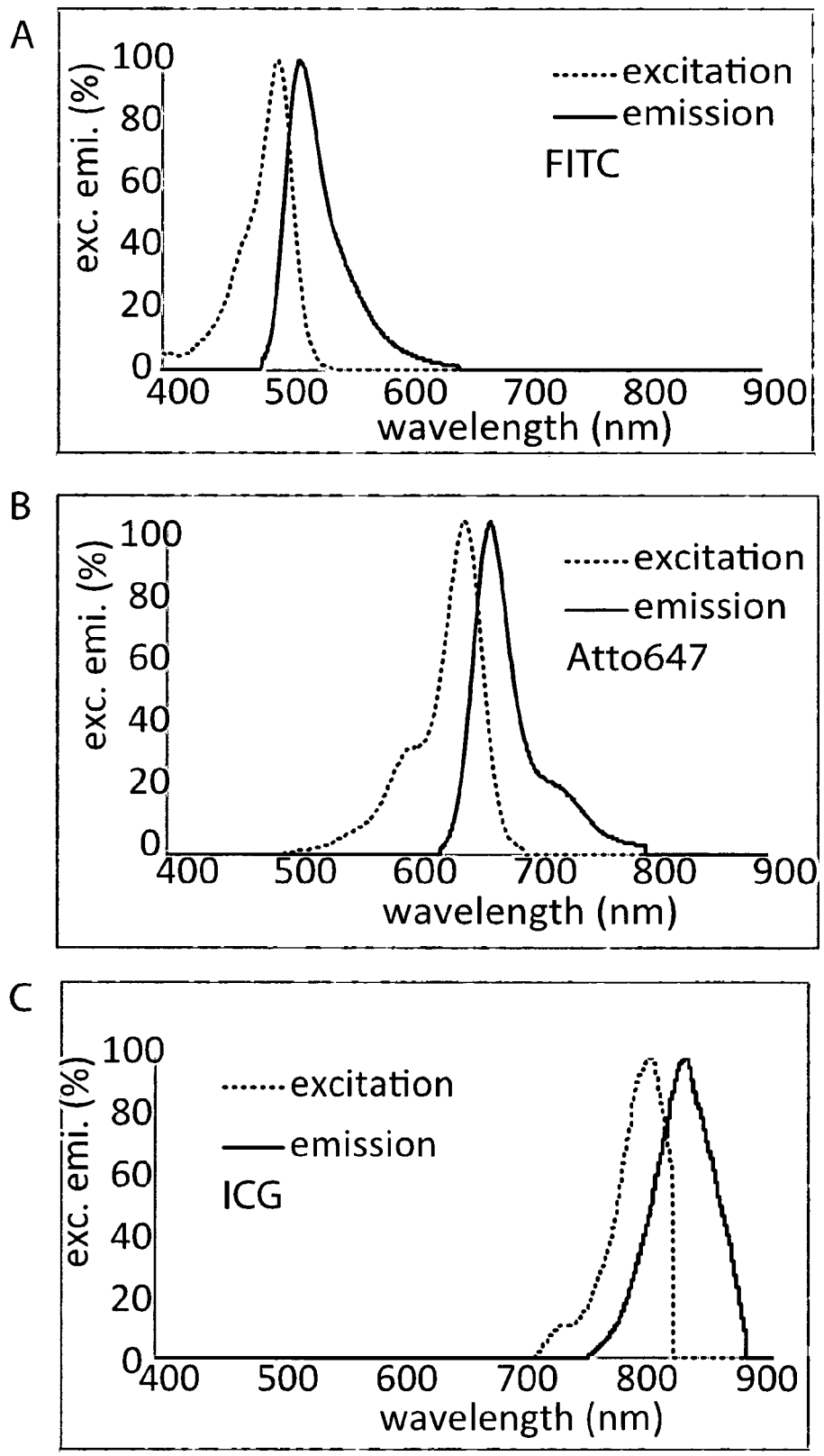

FIG. 7 discloses the excitation spectra and fluorescence emission spectra of typical fluorescence emission spectra of typical fluorophores like Fluorescein isothiocyanate—FITC (FIG. 7A), Atto647 (FIG. 7B) and Indocyanin Green—ICG (FIG. 7C).

The images that are recorded are then transferred from the sensor 213 to the processing unit 300 for a series of image processing operations, such as demonstrating, registration, noise filtering, background dark noise subtraction, color correction for the color frames, and spectral unmixing. In particular the spectral unmixing in the simplest form can be a linear transformation between the color channel images generated from the camera and the component space. Components can be anything that the light can carry information from, such as materials, concentrations or properties, or quantities that can be derivatives from those components. They may have a particular spatial distribution corresponding to elements 401, 402 of object 400. After the calculation of the images 501, . . . , 507 of the spatial distribution of the components 401, 402, and so on, they can be stored, displayed, or overlaid on other images, with the use of colormaps, such as pseudocolor.

Some examples for images after spectral unmixing, but not limited to this, show:

a) Absorber distribution: The spectrum of the reflected light is shaped by the absorption and transmission spectrum in the tissue of object 400, and this is recorded in the color sensor signals. By system and tissue modeling of tissue absorption and/or system calibration on absorbers with known concentrations, it is possible to derive the concentration of intrinsic tissue absorbers like oxygenated and deoxygenated hemoglobin, melanin, etc. or also externally administered absorption contrast agents, e.g. methylene blue.

b) Oxygen saturation: From the maps of the oxygenated and deoxygenated hemoglobin distribution it is possible to calculate an oxygen saturation map, and relevant physiological or pathological parameters.

c) Fluorochrome distribution: Fluorescence comes either from endogenous fluorochromes or externally administered fluorescent contrast agents. The fluorescence signals are recorded by the color sensor and by system and tissue modeling and/or system calibration it is possible to derive the fluorochrome distribution. Additionally, it is possible to calculate ratios between fluorochrome maps, which convey more specific information on cancer. In the following a basic description for image processing for the calculating the fluorescence components is presented. Similar values like reflectance absorption distribution, and derivative values are modeled and calculated similarly.

In the present invention, the camera measures the signal intensity of different color channels. This signal is created by the light intensity of the sum of all components, which are spectrally filtered by the transmission filters and additionally by the RGB color filters of the sensor 211 combined with the spectral sensitivity of the sensor 211 Assuming that the detector response is linear, the signal generated is:

$$S_{c \in \{color\}} = \int_{\lambda_{min}=0}^{\lambda_{max}=\infty} \sum_{f \in \{fluorescenct\ channels\}} I_\lambda(\lambda, f) * T(\lambda, c) d\lambda \ \forall \ c \in \{color\}$$

where $S_c$ is the signal in a specific spectral color c out of all combined color sensor images; for example {color}={R, G, B}. $I_\lambda(\lambda,f)$ is the spectral fluorescence channel intensity density. It depends on the wavelength and the fluorescence channel. Each fluorescence channel is characterized by a specific spectral light characteristic. In the simplest case the spectral light characteristic of a fluorescence channel of the imaging system corresponds to a fluorophore. In this case the $I_\lambda(\lambda, f)$ corresponds to the spectral emission spectrum of the fluorophore. In this case an exact value of $I_\lambda(\lambda, f)$ can be determined considering the fluorophore concentration, the fluorophores quantum yield and the spectral illumination light intensity. $T(\lambda, c)$ is the total transmission characteristics of the specific spatial color sensor or pixel which also exhibits the transmission characteristics of the optical system including the emission filter. Assuming that the fluorescence activity is located close to the tissue surface so that the fluorescence emission spectral profile and intensity are not strongly influenced by the tissue intrinsic absorption, and that other non-linear effects like quenching are negligible, then the spectral fluorophore intensity $I_\lambda(\lambda,f)$ can be written as $I_\lambda(\lambda,f)=c(f)*\Phi_\lambda(\lambda,f)$:

$$S_{c\in\{color\}} = \int_{\lambda_{min}=0}^{\lambda_{max}=\infty} \sum_{f\in\{fluorescenct\ channels\}} c(f)*\Phi_\lambda(\lambda,f)*T(\lambda,c)d\lambda \ \forall c \in \{color\}$$

where c(f) is the concentration of fluorophore f. In case the fluorescence channel f is used for reflectance imaging, c(f) is the intensity factor. Symbol for the concentration c is the same as the color channel index. $\Phi_\lambda(\lambda,f)$ is the molar spectral fluorescence intensity density describes the spectral profile of the emission of a fluorophore f. The intensity is scaled by the concentration of the fluorophore c(f). In case f is a reflectance channel, $\Phi_\lambda(\lambda,f)$ is the normalized spectral reflectance intensity of a channel with a spectral distribution.

As one example, $\Phi_\lambda(\lambda,f)$ could be the spectral response of the red receptor in the eye. This would lead to a natural color impression for this red channel. After rearranging the formulation $$S_{c\in\{color\}} = \sum_{f\in\{fluorescenct\ channels\}} c(f) * \underbrace{\int_{\lambda_{min}=0}^{\lambda_{max}=\infty} \Phi_\lambda(\lambda,f)*T(\lambda,c)d\lambda}_{M(f,c)} \ \forall c \in \{color\}$$

leads to the linear relation between fluorophore concentration and measured channel intensity of the sensor:

$$S_{c\in\{color\}} = \sum_{f\in\{fluorescenct\ channels\}} c(f)*M(f,c) \ \forall c \in \{color\}$$

This linear relation allows computing all fluorescent and reflectance channel intensities c(f). Herein, there is an example of the calculation of the matrix M for a sensor with the channels red, green and blue and the dyes fluorescein isothiocyanate (FITC), Atto647 and Indocyanine green (ICG). The fluorophore excitation and emission spectra are given in FIG. 7:

The signal equations are:

$S_{red} = c(FITC)*M(FITC,red) +$
$\quad c(Atto647)*M(Atto647,red) + c(ICG)*M(ICG,red)$ $S_{green} = c(FITC)*M(FITC,green) +$
$\quad c(Atto647)*M(Atto647,green) + c(ICG)*M(ICG,green)$ $S_{blue} = c(FITC)*M(FITC,blue) +$
$\quad c(Atto647)*M(Atto647,blue) + c(ICG)*M(ICG,blue)$ $$\begin{pmatrix} S_{red} \\ S_{green} \\ S_{blue} \end{pmatrix} = \begin{pmatrix} M(FITC,red) & M(Atto647,red) & M(ICG,red) \\ M(FITC,green) & M(Atto647,green) & M(ICG,green) \\ M(FITC,blue) & M(Atto647,blue) & M(ICG,blue) \end{pmatrix} * \begin{pmatrix} c(FITC) \\ c(Atto647) \\ c(ICG) \end{pmatrix}$$

With the coefficients M exemplary written for the combination of FITC and the red detector channel:

$$M(FITC,red)=\int_{\lambda_{min}=0}^{\lambda_{max}=\infty} \Phi_\lambda(\lambda,FITC)*T(\lambda,red)d\lambda.$$

The fluorescence intensities can be obtained by inverting the coefficient matrix M:

$$\begin{pmatrix} c(FITC) \\ c(Atto647) \\ c(ICG) \end{pmatrix} = M^{-1} * \begin{pmatrix} S_{red} \\ S_{green} \\ S_{blue} \end{pmatrix}$$

If, in a preferable embodiment, the number of detector color channels is equal to the number of fluorescent channels to be resolved, the equation system can be solved as a linear system of equations. The variables $S_c$ are measured by the imaging system. The values of c(f) can be calculated if the other parameters of the system are known ($\Phi_\lambda(\lambda,f)$ and T($\lambda$, c)). These factors and therefore the matrix M(f, c) can be determined in advance in a calibration process. In order to calculate c(f) the matrix M(f, c) needs to be inverted.

If the number of measured channels is bigger than the number of fluorescence channels, the system is over-determined. One option to handle this favorable situation is to compute the pseudo-inverse of M(f, c) which is not anymore a square matrix. Various algorithms may be used to improve the outcome of the calculation and for example minimize noise originating from the measurements in the sensors.

The matrix M can be either calculated from system modeling and/or from system calibration. In system modeling, the light path spectral content can be modeled from the light source to the color sensor array pixels. Parameters include but are not limited to illumination source spectral distribution, the spectral transmission of the excitation filters, or the spectral profile of the illumination lights, the fluorochrome excitation and emission spectra and the quantum yield, the approximate depth of the components in tissue, the optical properties of tissue, the transmission characteristics of the imaging system (lenses, beam splitters, filters, mirrors, etc.) and/or the spectral sensitivities of the sensor array. The modeling calculates the matrix M that associates the concentration information with the recorded signals (forward problem). The component distribution can be derived from the solution of the inverse problem. Alternatively, system calibration can be done with either recording of the signals of components of known composition, concentration and location, and then solving for the unknown matrix M, or by a blind decomposition with unmixing algorithms, such as Principle Component Analysis (PCA), Independent Component Analysis (ICA), or similar statistical algorithms. Finally, modeling or in general the use of prior information can be used to determine more unknown parameters than the number of measured channels.

Alternatively to the linear modeling the system can be modeled in more detail using a non-linear description. In this way it is possible to take into account the potential of non-linearities, such as the detector or the quenching effect of high fluorochrome concentrations. Finally, with modeling and/or prior information it is possible to calculate a matrix that recovers the information from more components than the number of available channels in what would otherwise be an underdetermined system.

[Number of Spectral Bands]

Finally, as described before, the number of components unmixed is related to the number of channels (e.g. colors) available from the sensor, or, in case of combined images, the total number of color channels of the combined images. However, the number of spectral bands in the illumination and/or the transmission is independent from the number of channels (colors) and the number of components unmixed. In general the more bands are available in the region of interest, the less likely is that a spectral feature from a particular component will not be recorded. Thus, many "narrow" spectral bands offer more accurate color representation of the reflectance image, and more accurate unmixing of the various components. Yet, spectral unmixing of various components is feasible with a number of spectral bands that is smaller than the number of channels.

It is important to highlight, that the number of spectral bands of multiband filters is not a relevant mathematical condition for the number of fluorophores to be unmixed. Instead the number of camera channels is the mathematically important condition.

EXAMPLE 3

In the following, we describe a basic light source useful for the present invention and various alternatives.

Figure 8:
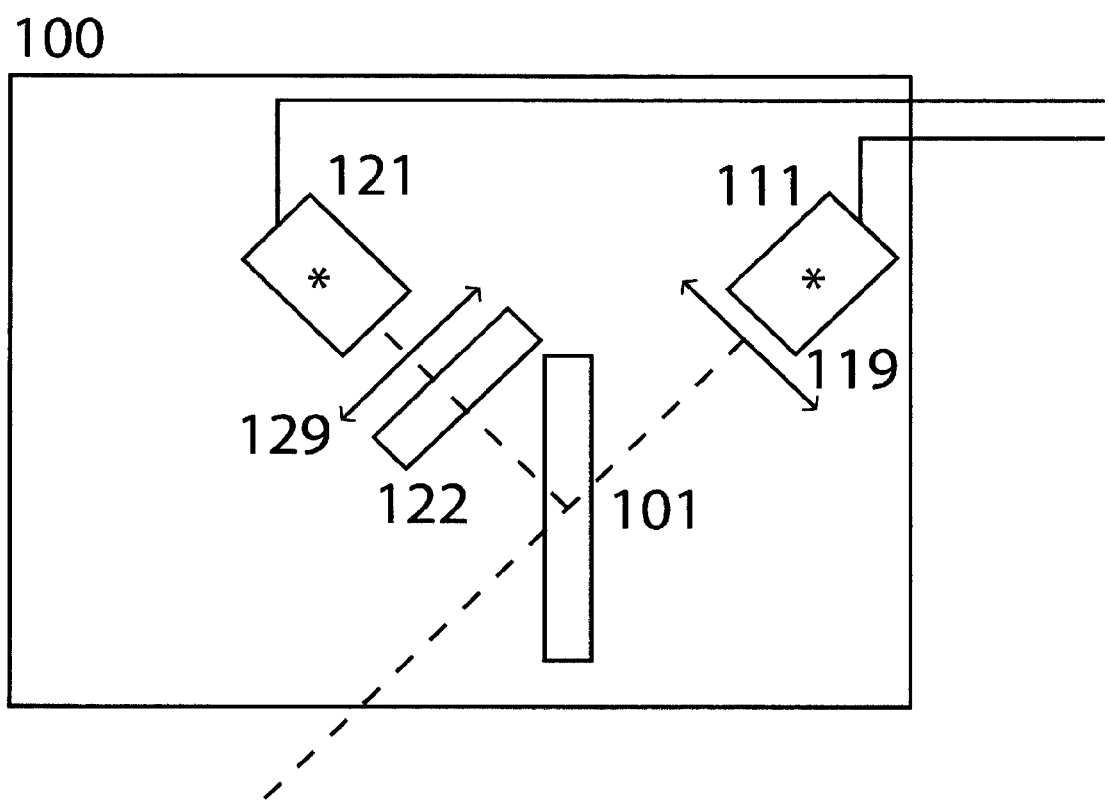
Figure 9:
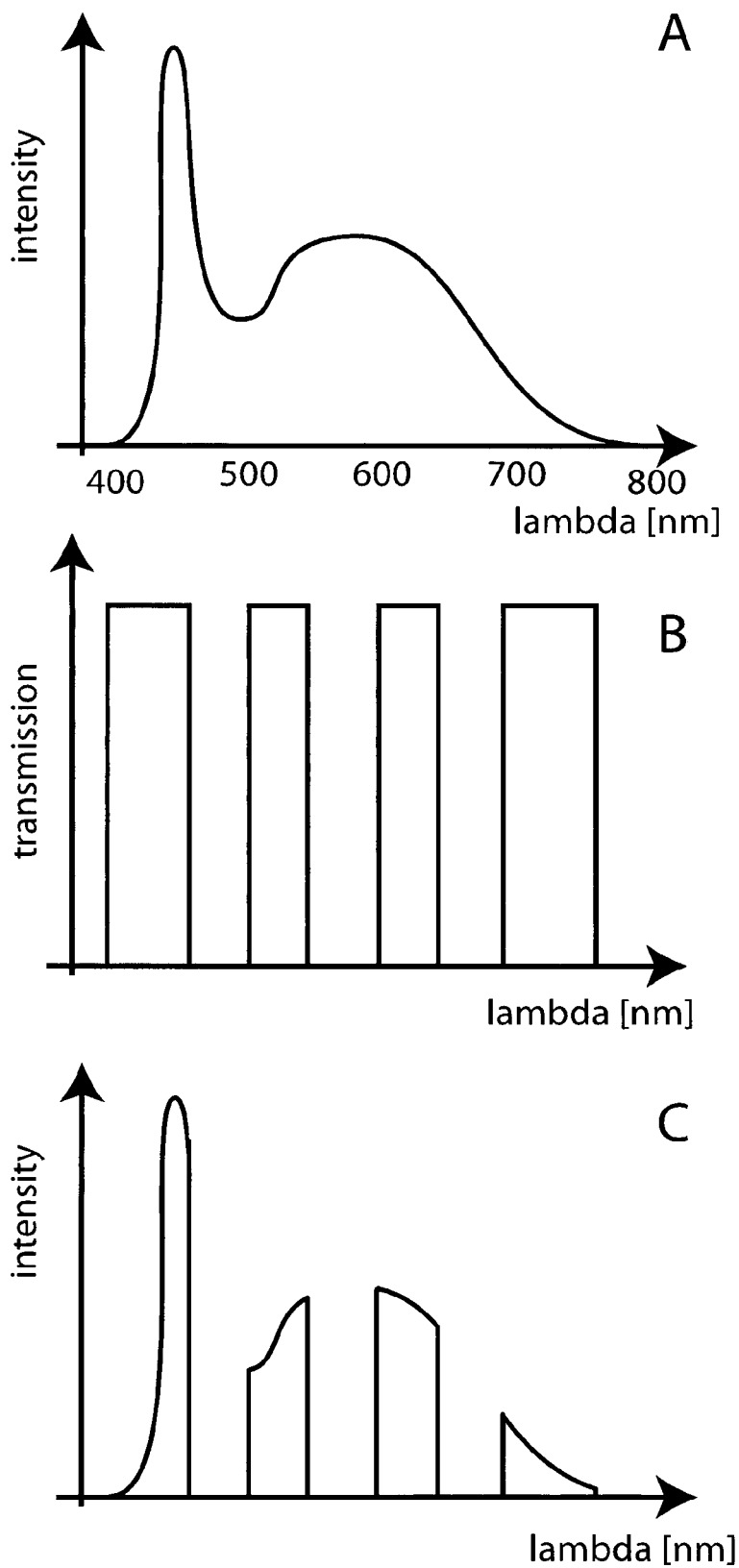
Figure 10:
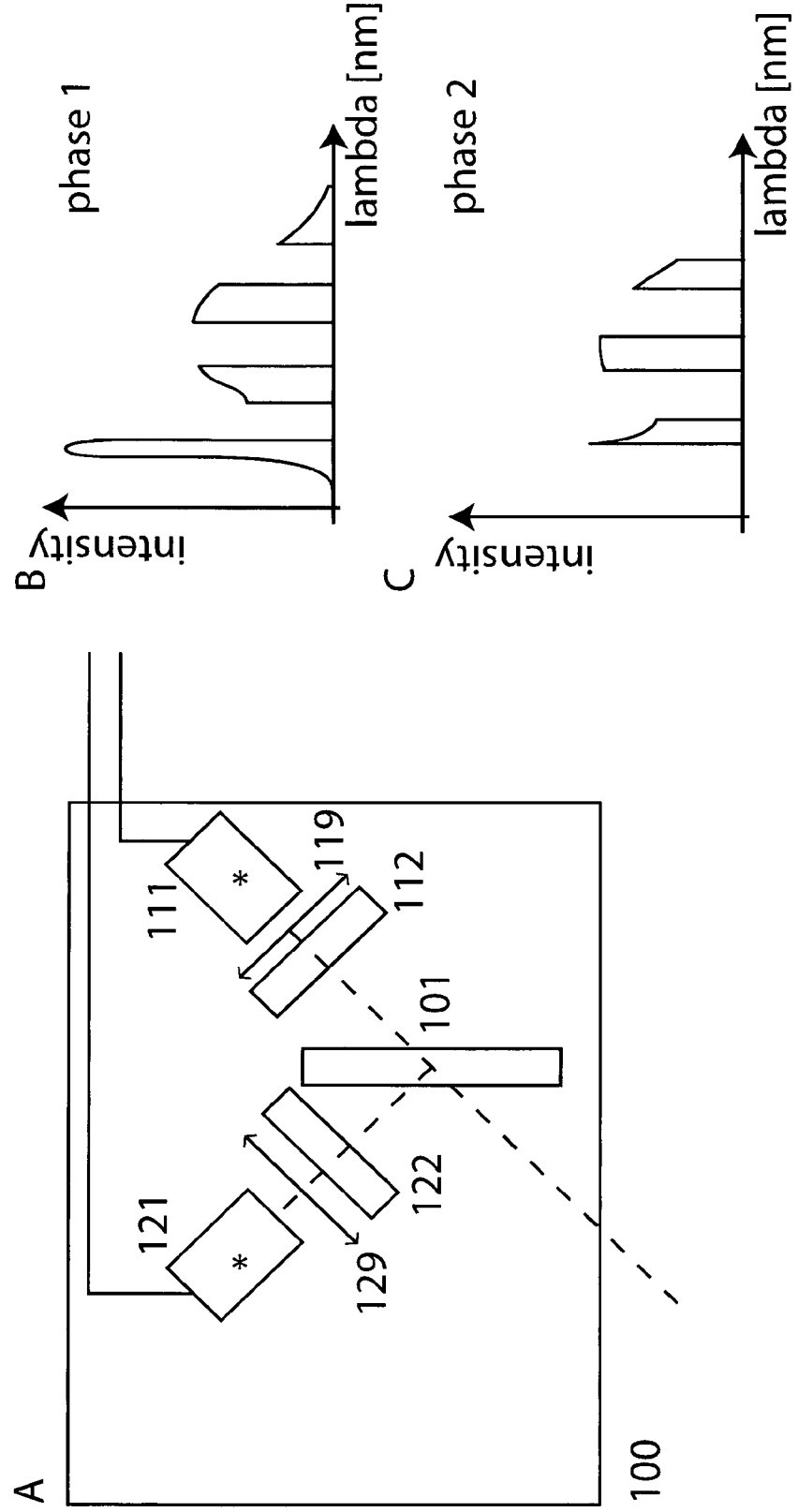

As previously described and as shown in FIG. 8 the most basic light source 100 consists of two separate light sources 111, 121, which are preferably broadband LEDs 111 and 121. LEDs generally have very fast switching performance compared to conventional light sources such as Halogen or Xenon lamps. The beams are optionally collimated with collimation lenses 119 and 129. Light emanating from source 121 is filtered by bandpass filter 122 and then combined with light emanating source 121 using a polychroic mirror 101.

FIG. 9A shows the spectrum of the broadband LEDs, that can be the same or different for light source 111, 121. The spectrum is typical for a white light LED. FIG. 9B shows the transmission spectrum of the multi-band excitation filter 122. FIG. 9C provides an intensity spectrum of the light emitted by LED source 121 and filtered by filter 122.

In a preferable embodiment the emission spectrum of the two broadband high power LED sources with a maximum spectral power density is more than 30 mW/nm. The emitted light is filtered by a multi-bandpass filter as shown in FIG. 9B. The filter has transmission bands (420-460 nm, 510.5-531.5 nm, 590-624 nm, 677.5-722.5 nm) with an approximate maximum transmission of 90% in each transmission band. The attenuation characteristics of the filter in the blocking regions are typically at least of optical density 2 (O.D. 2). Usually the out of band rejection/attenuation characteristics of the filters are as good as O.D. 6.

The effective emission of the light source after filtering with the respective multi-band filter is illustrated in the FIG. 9C. The spectrum of the first light (source 121) is shaped by the filter during this illumination phase and the spectrum of the second light (source) is the intrinsic broad-band emission profile as shown in FIG. 9A or a similar broadband. Thus all the drawn spectra of light are accumulated spectra during the respective phase.

One potential disadvantage with this basic light source is that the illumination field might not be optimal for the visual perception of an observer both in terms of intensity and of spectral content. The two lights have different overall intensity and spectral content and when they are alternating may present a visual flickering of intensity or color. Additionally the spectral content is not balanced and the color appearance may not be natural.

An alternative illumination source is a variation of the basic light source, with the difference being that the second light is also filtered with a filter 112 as shown in FIG. 10A. The basic advantage of filtering the second light is that it facilitates the optimization of the overall color perception and minimizes the flickering. The filter 112 may also be a multiple bandpass filter. Its spectral transmission characteristics may be complementary to that of the filter 122 and may have the same or similar transmission characteristics to the fluorescence emission filter 213 in front of the sensor array 211. FIG. 10B provides the spectrum of the first excitation light in a first phase as emitted by the light source 121 after filtering by filter 122. FIG. 10C provides the spectrum of the second excitation light in a second phase as emitted by the light source 111 after filtering by filter 112. The complementary filters 112 and 122 accumulatively provide a spectrally continuous illumination that is almost equal to a broadband illumination by the original broadband source thus providing natural color perception. Additionally the effect of intensity or color flickering is less. Nevertheless, the spectral shape of the light illumination of the second light (phase 2) may freely be modified in order to achieve optimum color perception and minimal intensity flickering.

Additionally the output of the light source 100 can be coupled into a light guide by a fiber coupling lens system. This light guide can either be a single optical fiber, a fiber bundle, or a liquid light guide.

Figure 11:
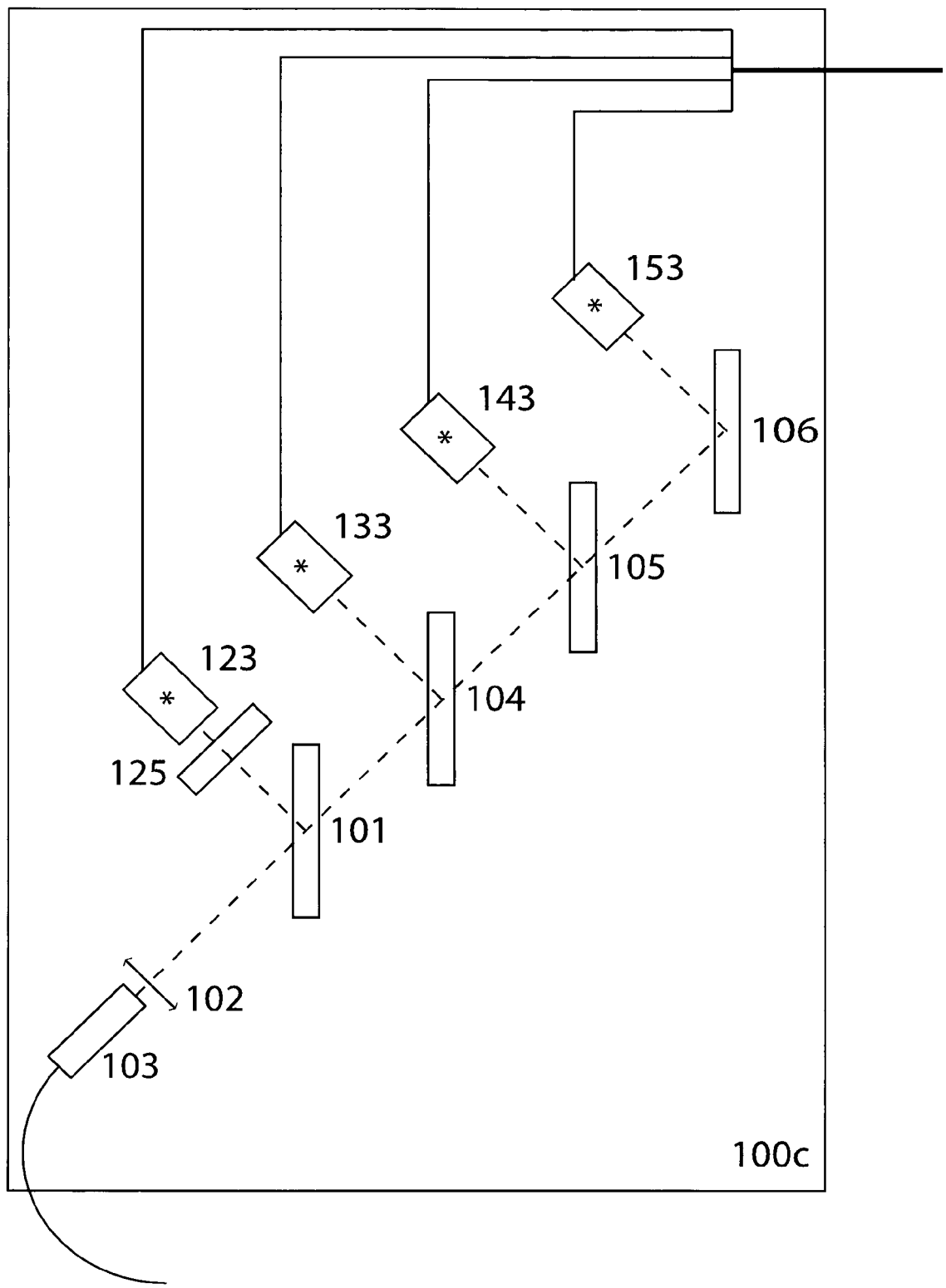

In an alternative implementation of an illumination system as shown in FIG. 11 one or more of the broadband light sources that are filtered with the multiband filters is replaced with a set of narrowband individually controlled sources 133, 143, 153 optionally filtered by respective narrow band filters 125. Such sources 133-153 can be lasers, laser diodes, LEDs, etc. In FIG. 11 the light emitting module 111 of FIG. 10A has been replaced by multiple laser sources 133,143, 153. The emitted light of the module 123 is filtered by the filter 125. The polychroic mirrors 101, 104, 105, 106 combine the radiation of lasers 133, 143, 153 with the radiation from laser 123. All the lights are coupled together into a fiber 103.

The beam splitter 101 may be a polarization beam splitter. In this way the different sources 123, 133, 143, 153 can be combined minimizing the losses. Multiple lasers 133, 143 and 153 and more may replace one broadband source, e. g. source 111 in FIG. 10. The lasers 133, 143, 153 may have a narrow spectral emission profile and/or might be tunable. Some lasers may require a cleanup filter to suppress unwanted amplified spontaneous emission. The lasers may also be tunable in wavelength and intensity, they may be continuous wave lasers or pulsed lasers. The different laser sources are combined by longpass polychroic mirrors 104 (cutoff wavelength 415 nm,) 105 (cutoff wavelength 650 nm) and 106 (plain mirror with high reflectivity around 785 nm). These, or similar, narrowband sources comprising the illumination in one phase may illuminate simultaneously, with full or partial time overlap, or may operate sequentially. Nevertheless, any time combination within the exposure period associated with an illumination phase is considered as an accumulative light spectral distribution in one illumination phase.

Figure 12:
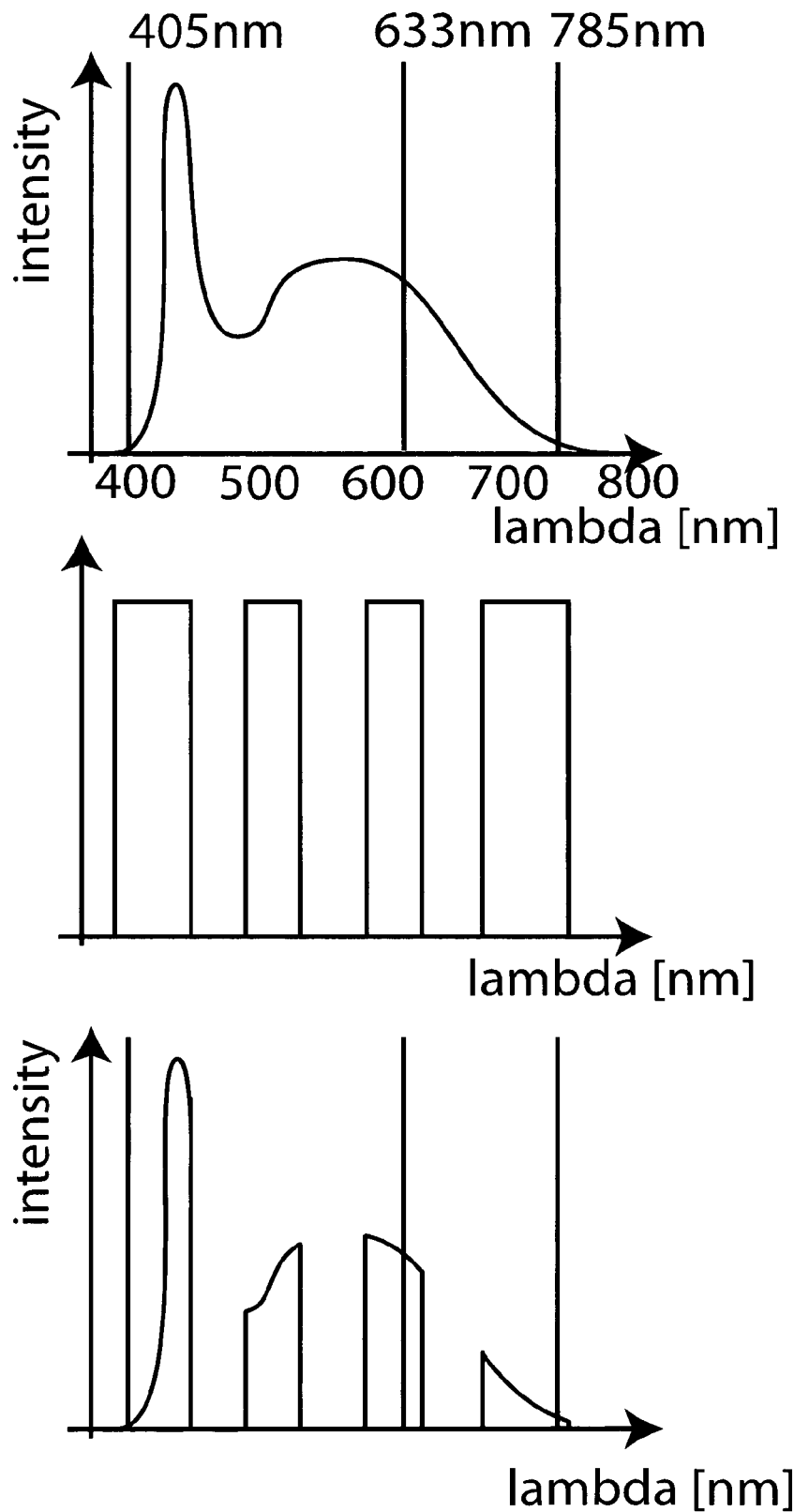

A preferred spectral scenario is illustrated in FIG. 12 where a broadband LED source covers the entire spectral range and is combined with narrowband laser sources which are may preferably be (for switching reasons) laser diodes. In this case popular modules like 405 nm, 633 nm and 785 nm laser diode modules are used. The diode laser at 405 nm can excite protoporphyrin IX (PPIX) which is widely used for brain surgery. The diode laser at 633 nm can excite a highly stable and bright fluorophore such as Alexa647 used in fluorescent probes, and the diode laser emitting at 785 nm excites the clinically relevant indocyanine green (ICG).

EXAMPLE 4

Figure 13:
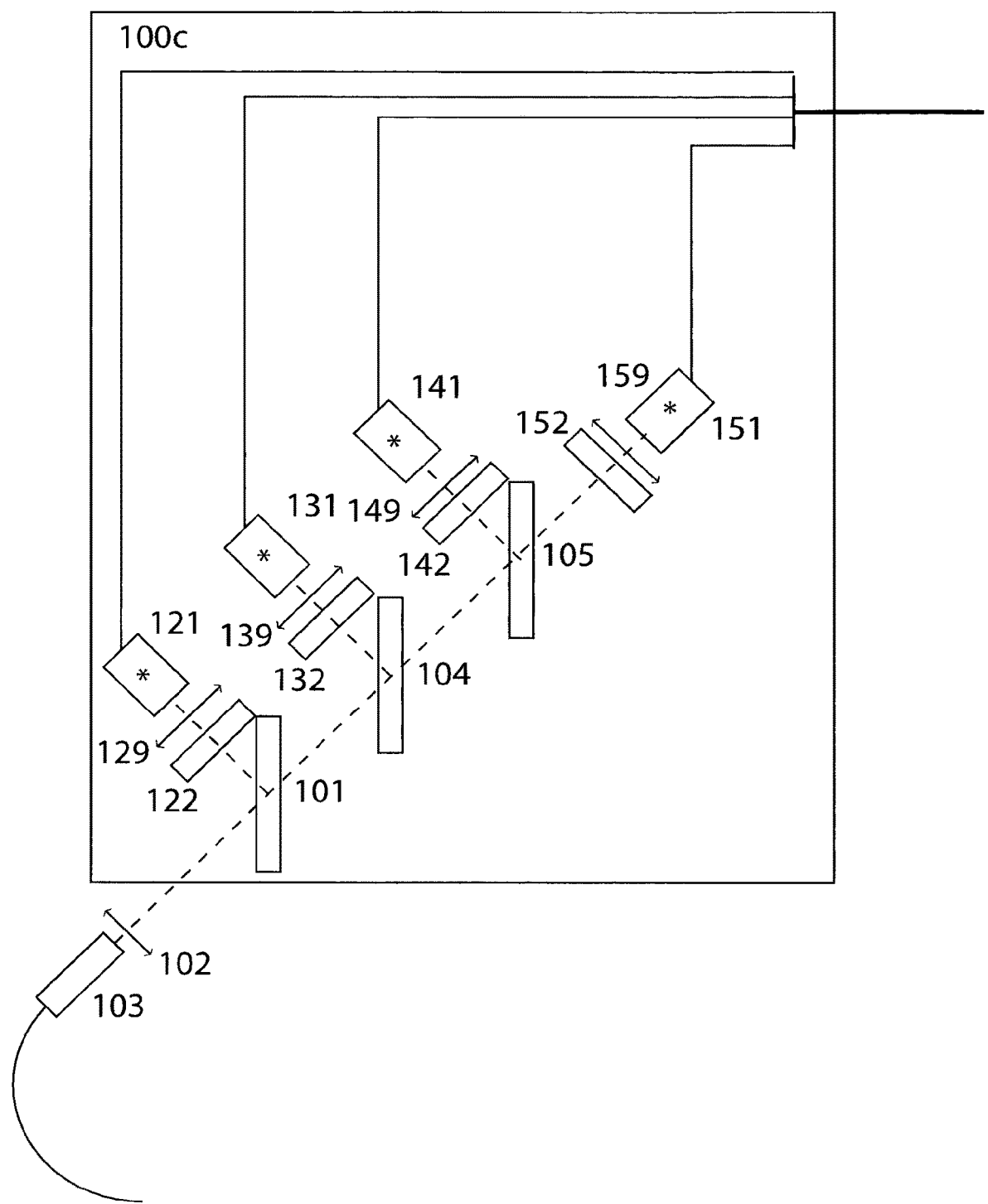

In this example an alternative illumination system is used for generating the illumination lights with several LED light sources. As shown in FIG. 13, instead of using two broadband LED sources this option uses multiple LEDs 121, 131, 141, 151 . . . that have a narrow spectral emission. This requires a more complicated lighting device, but on the other hand the output power can be increased dramatically and the intensity of the different LEDs can be balanced independently. Most monochrome LEDs still have a narrow emission with tails on the side spectrum. Thus excitation filters 122 132 142 152 may be optionally used in front of each LED to clean up the excitation spectra. Similar to laser sources, the light from an LED source comprised of many narrowband sources may be regarded as one illumination light. The LEDs can illuminate simultaneously, with full or partial time overlap, or may operate sequentially with no overlap. Nevertheless, any time combination within the exposure period associated with an illumination phase is considered as an accumulative light spectral distribution in one illumination phase.

Figure 14:
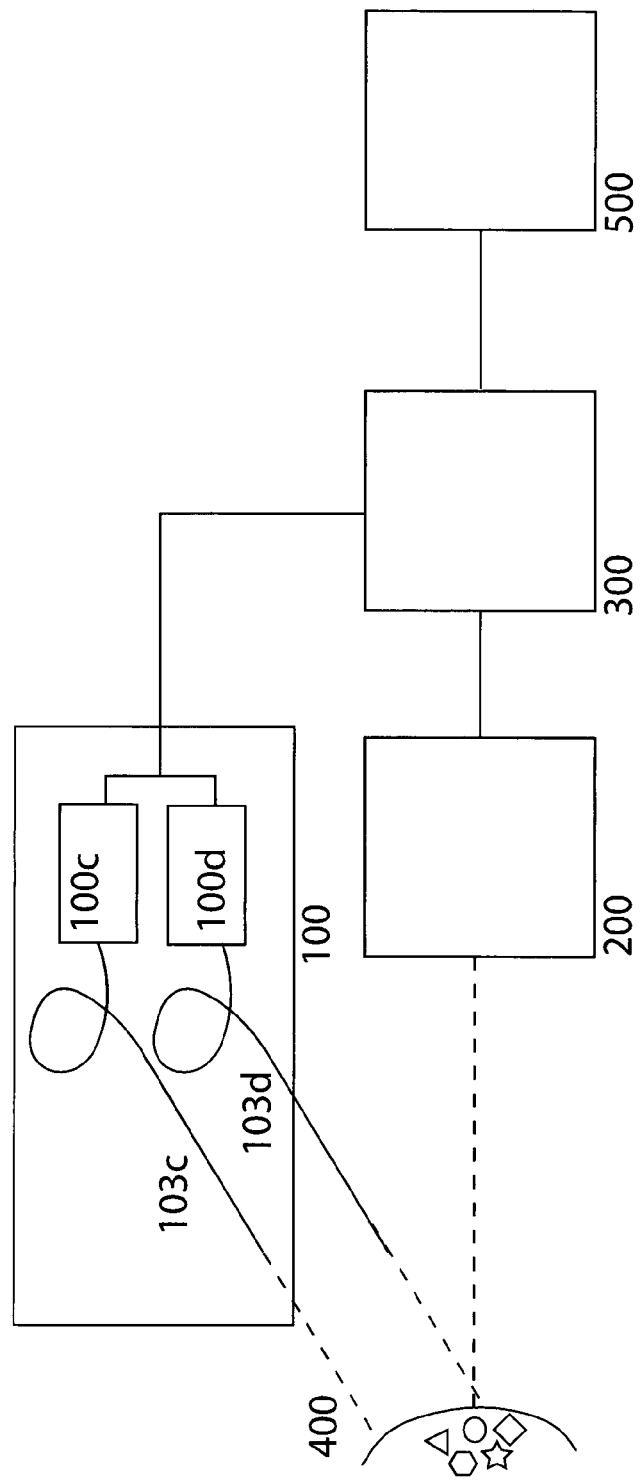
Figure 15:
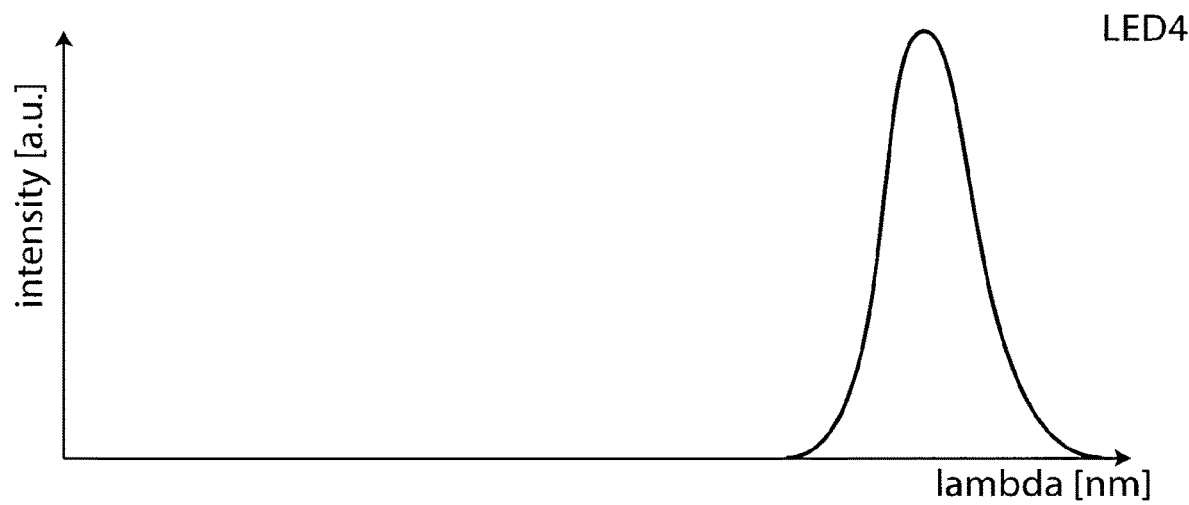
Figure 15:
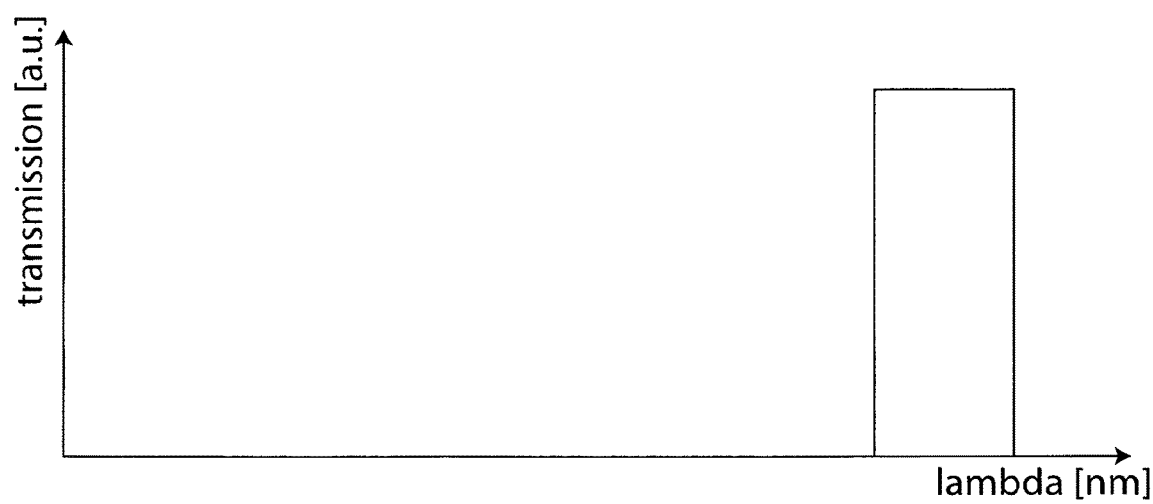
Figure 15:
Figure 16:
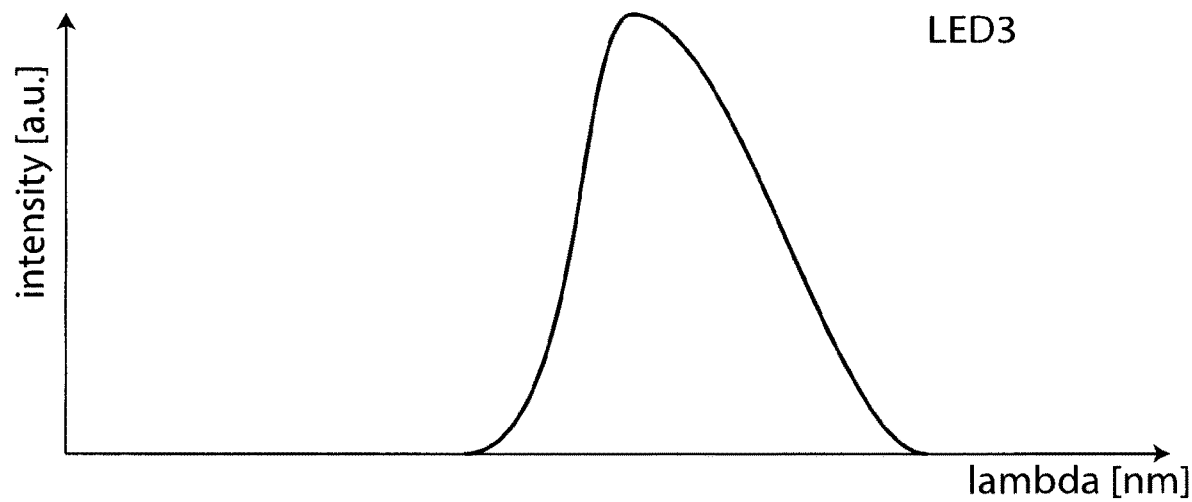
Figure 16:
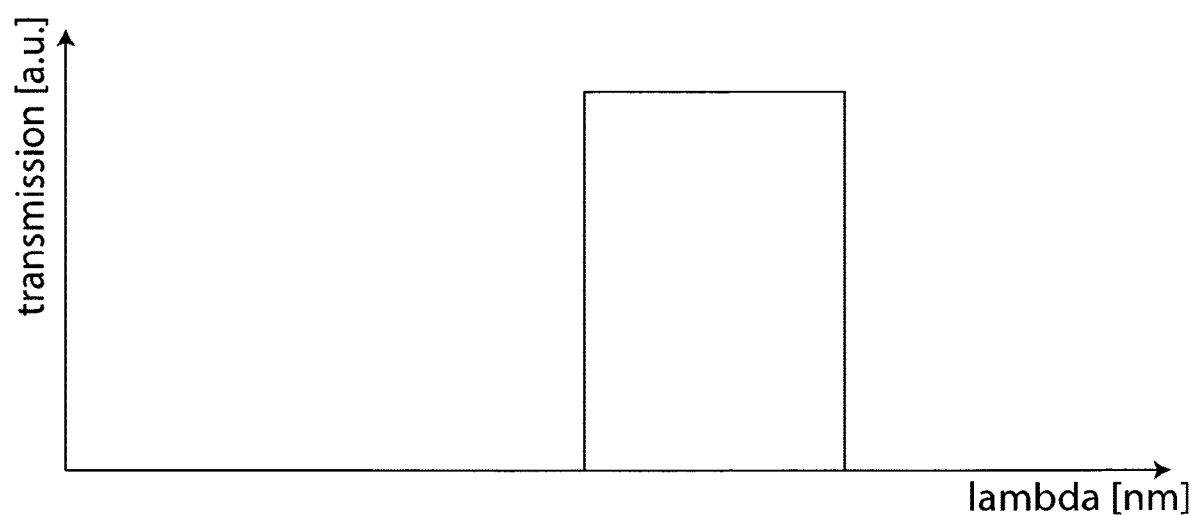
Figure 16:
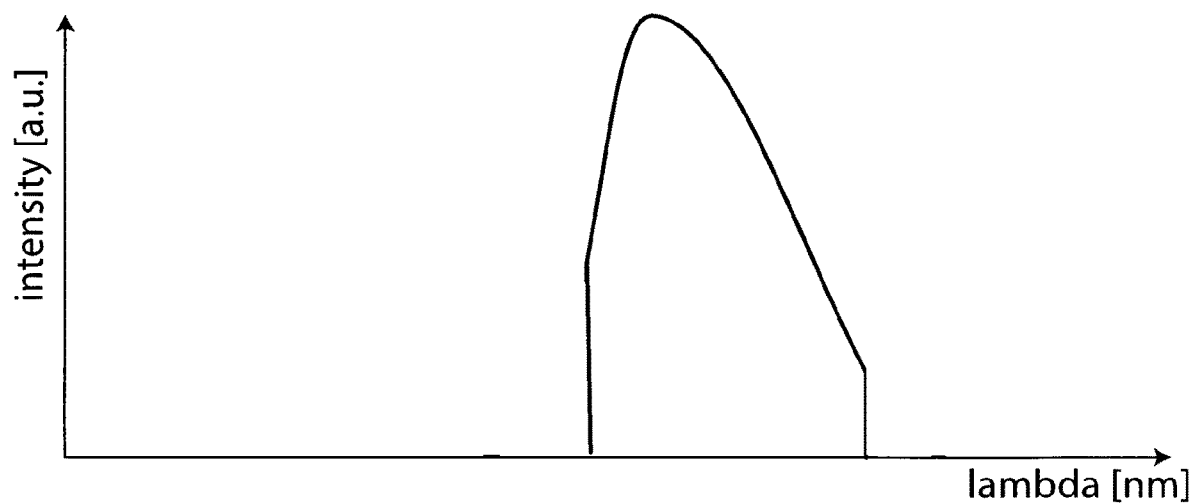
Figure 17:
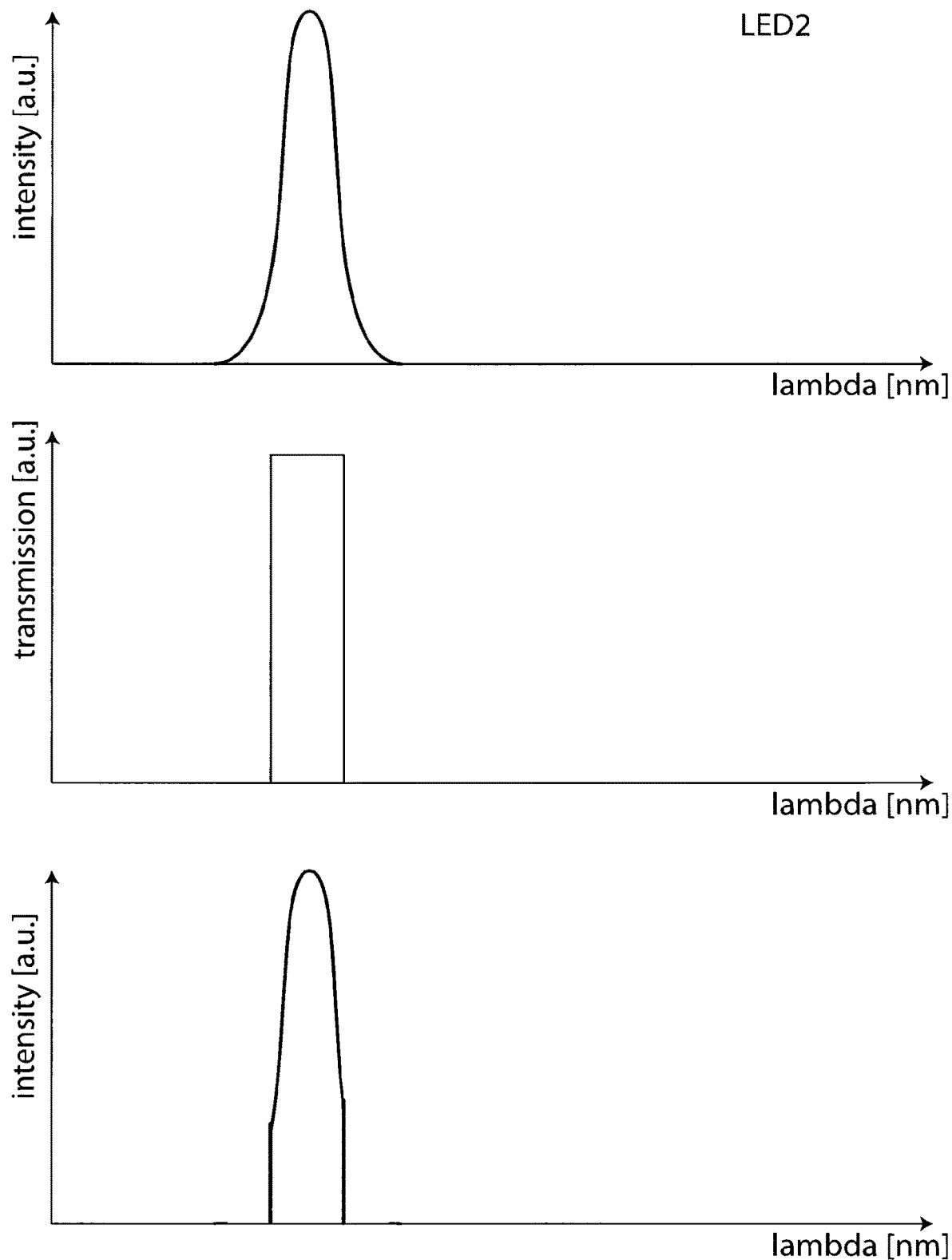
Figure 18:
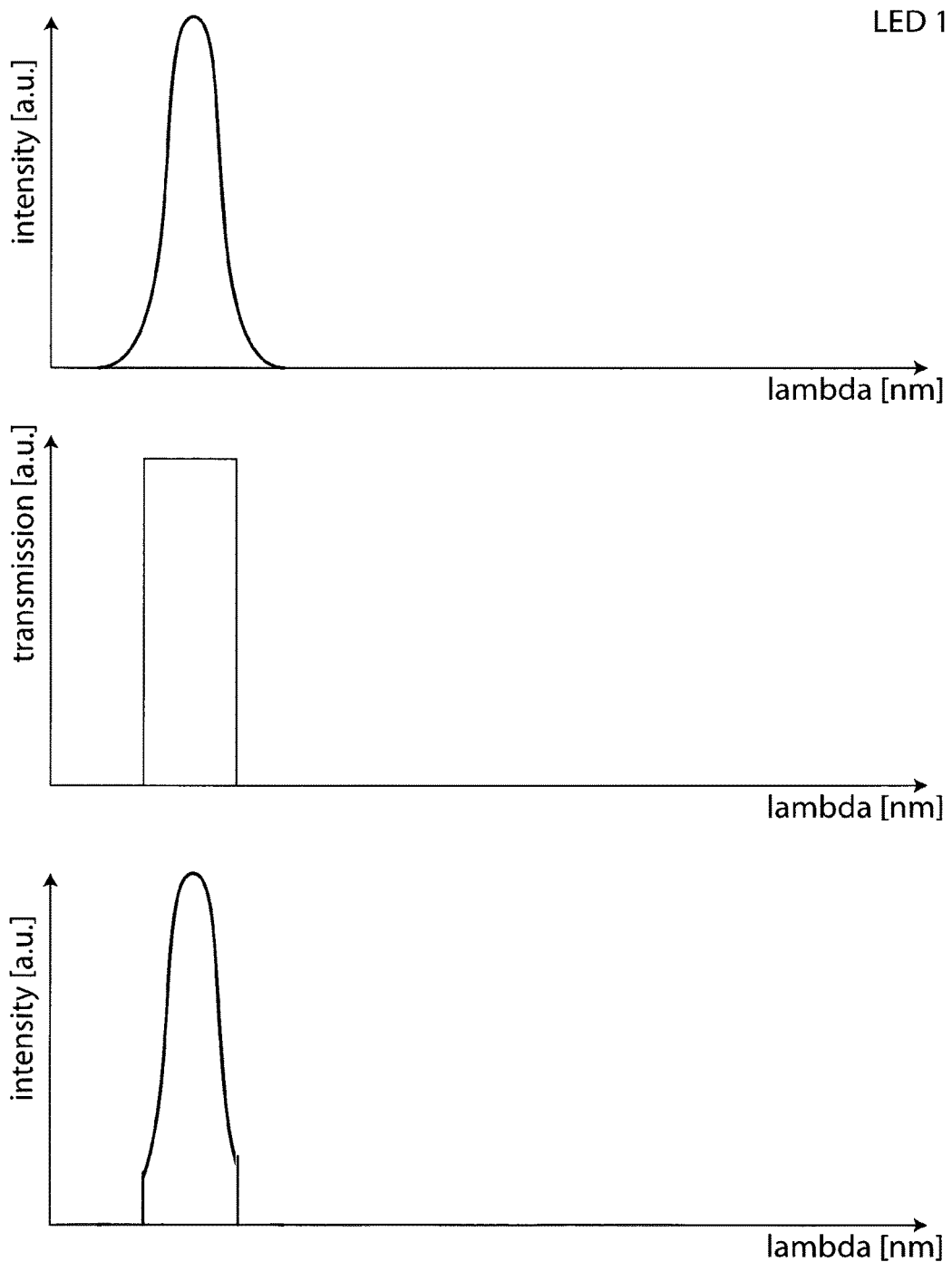

Such illumination sub-systems like the one described in FIG. 13 can be combined in a multiphase illumination system as shown in the schematic of FIG. 14. Therein, two light sources 100 c and 100d are provided, each coupling its emitted light into fibers 103c and 103d, respectively for illumination of sample 400.

FIGS. 15 to 18 show each an emission spectrum of an LED light source, a transmission spectrum of a filter arranged in the emitted beam and an intensity spectrum of the emitted light after passing said filter. All four light sources together may replace one spectrally broadband light source.

Figure 19:
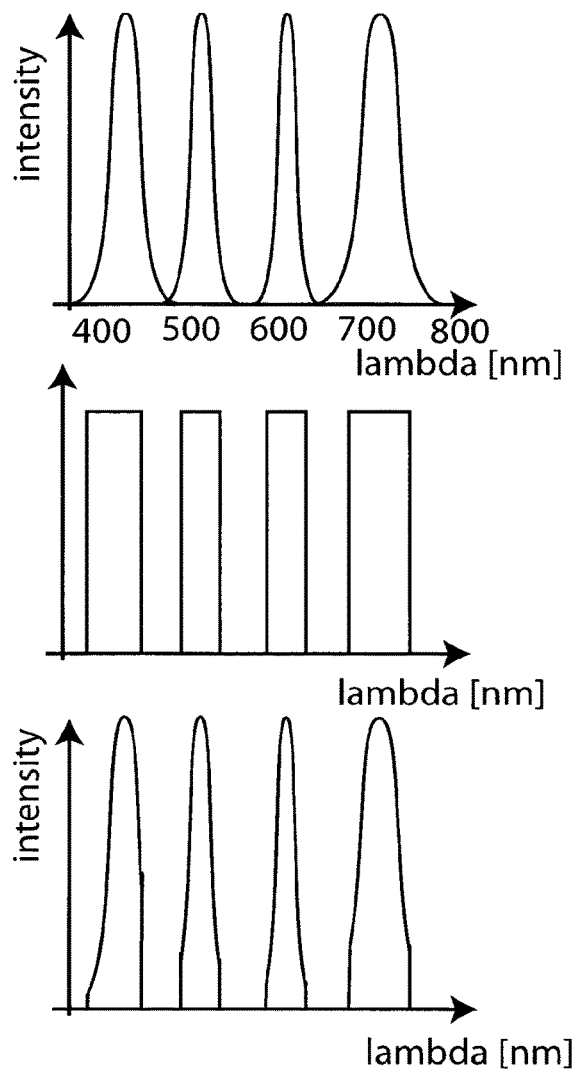
Figure 19:
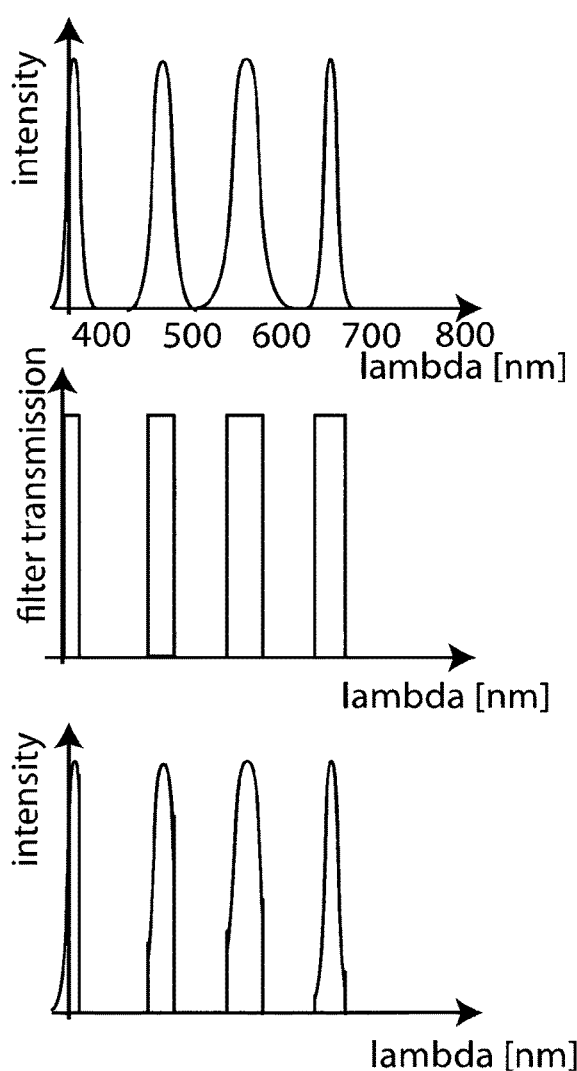
Figure 20:
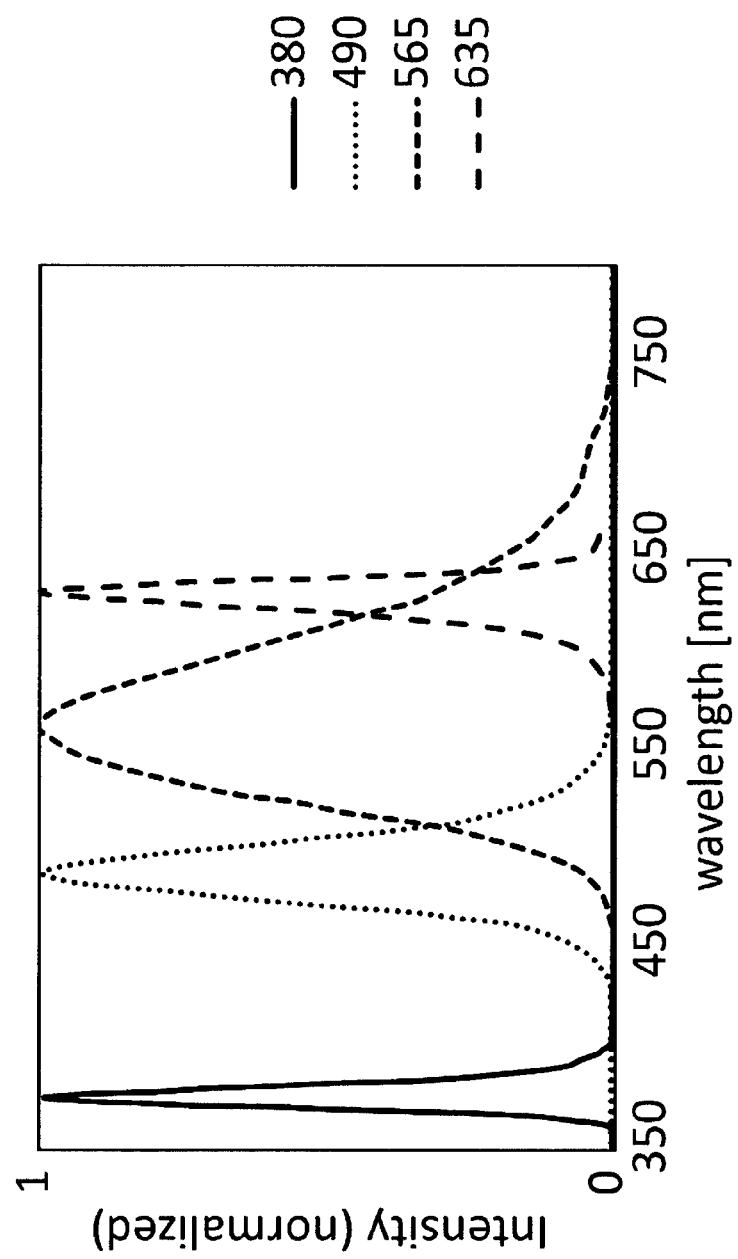
Figure 21:
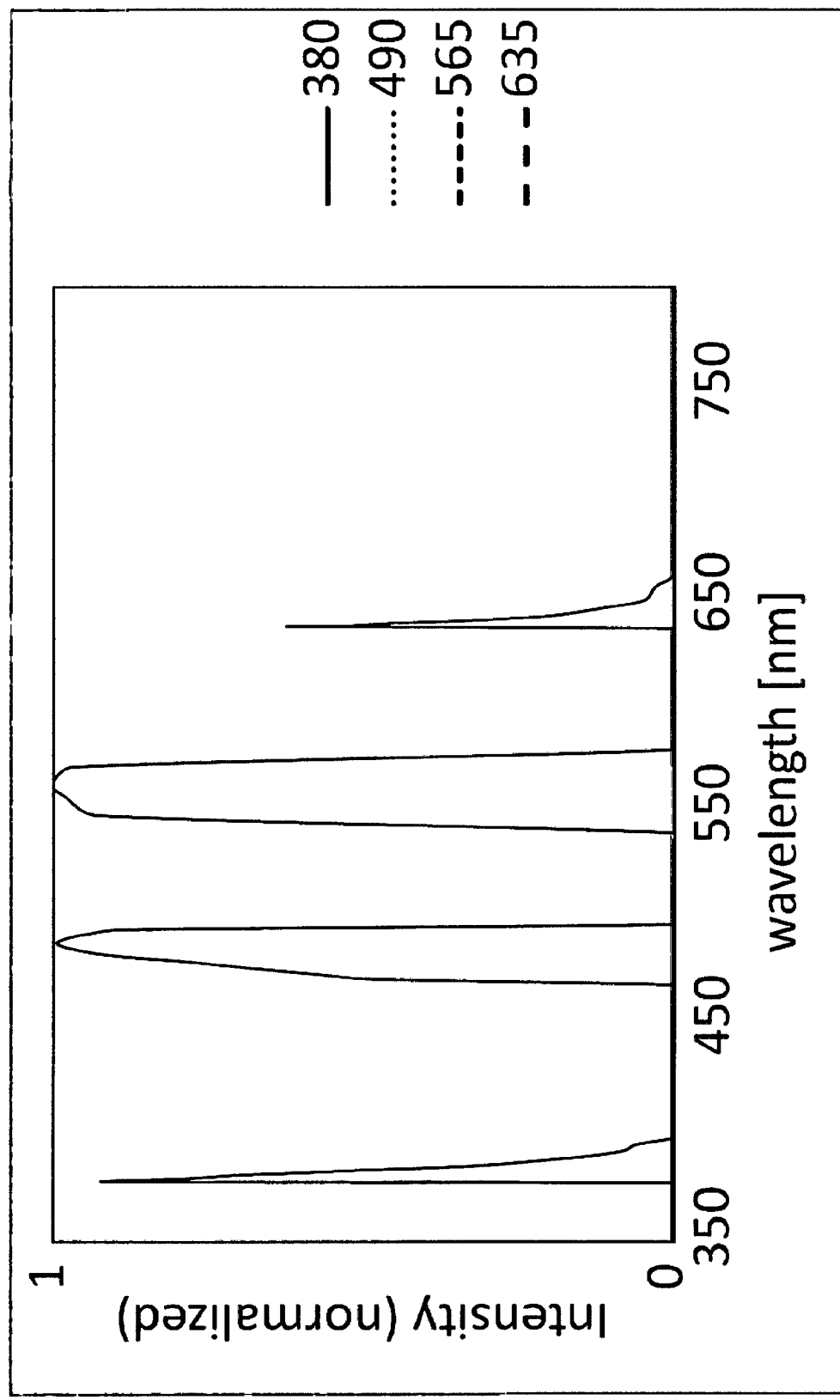

This preferred configuration has one excitation LED for each band of the multi-band filters. This would require 8 single different LEDs for quadruple band-pass filters. The spectra of such a configuration are shown in FIG. 19. FIG. 19 shows on the left side the spectrum of 4 LEDs, which constitute the first light source, the transmission spectrum of the corresponding filter and the resulting emission spectrum of the first light. On the right, corresponding spectra for the second light are shown. In the spectra, it is already implied, that each of the LEDs is associated with one light and thus with one phase. Though, the set of 4 individual LEDs can also be filtered using 4 individual single bandpass filters in front of each individual LED. Also the individual LEDs do not be strictly connected to one of the phases. FIG. 20 shows the real emission spectra of 4 commercially available LEDs with emission maxima at 380 nm, 490 nm, 565 nm, and 635. FIG. 21, shows the resulting illumination spectral profile of the above four LEDs filtered by a quadruple band pass filter.

EXAMPLE 5

Figure 22:
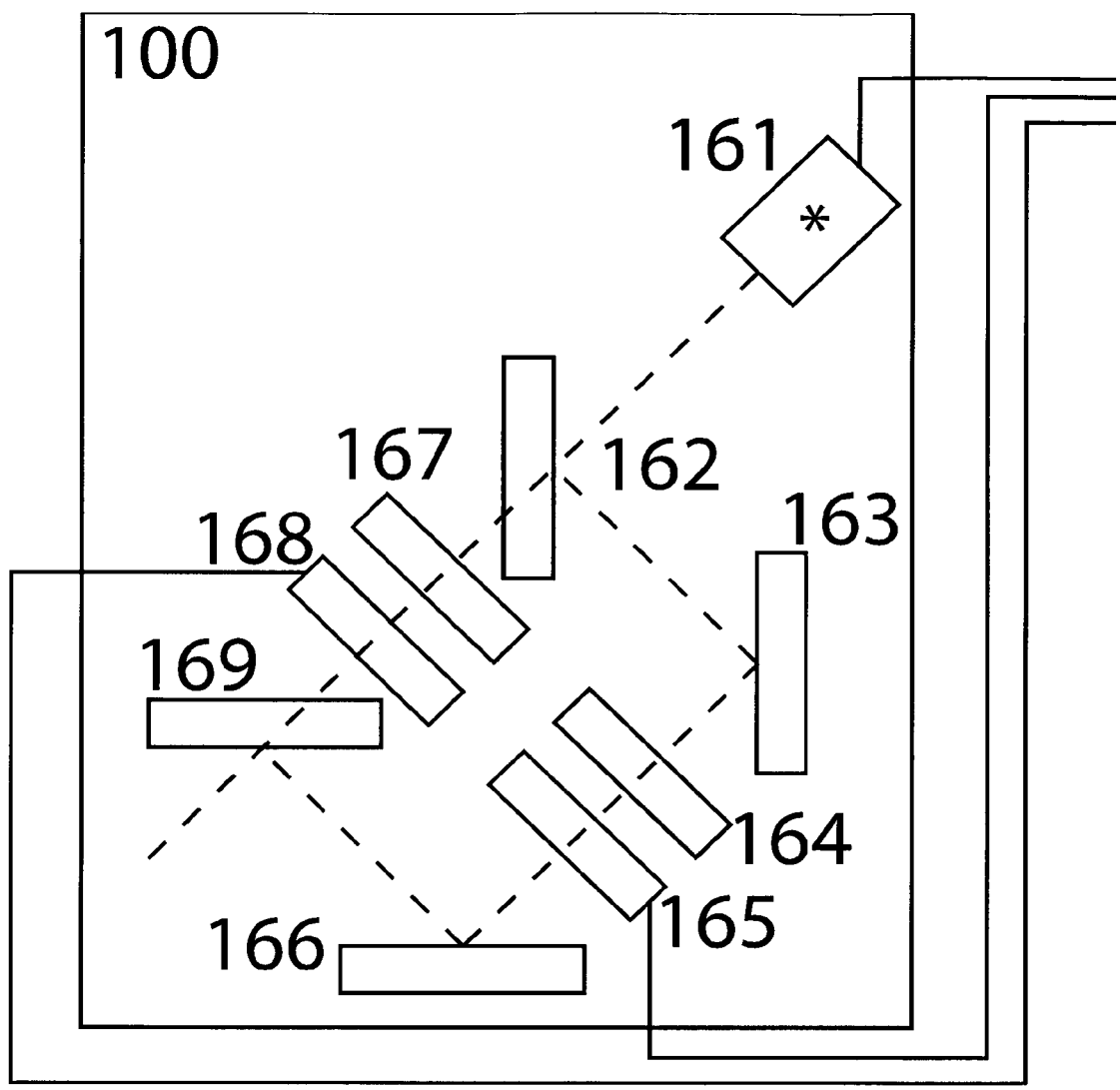

In a further example shown in FIG. 22, temporal switching between different light sources is performed using optical elements 168 and 165 with variable transparency. In the simplest case these elements 168 and 165 with variable transparency are mechanical shutters. They can also be light modulators or acousto-optical devices. The broadband light emanating from a light source 161 is split by a polychroic mirror 162, then filtered by complementary excitation filters 164 and 167 and merged again by a polychroic element 169 similar to element 162. Mirrors 163 and 166 are used to align and guide the partial beam filtered by filter 165 in the system. For further improvement, the excitation light should be collimated to minimize losses and optimize filter performance in the system.

EXAMPLE 6

Figure 23:
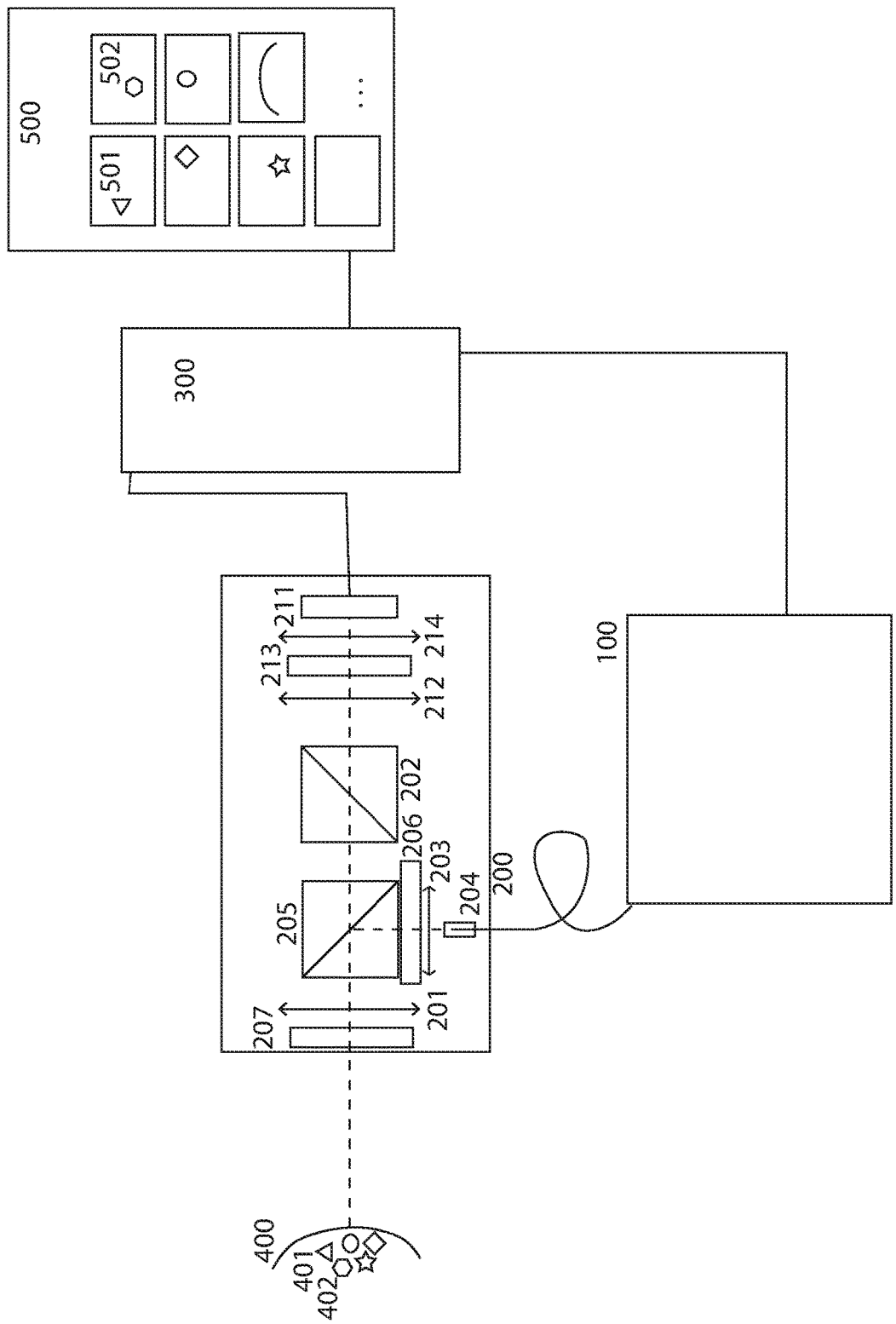

In an alternative embodiment as shown in FIG. 23 the illumination system is configured to illuminate through the optical system. An optical light guide delivers the light from the multispectral illumination system 100 into a part of the imaging device 200 at a connector port 204. The illumination path may contain an optical lens system 203 to optimize the illumination on the object 400. The light is then filtered by a polarization filter 206 and subsequently combined with the imaging path with a beam-splitter device 205. Such a device can be a polarization beam splitter cube 205. The light is then passed through a rotatable half wave plate 207 which is rotating the angle of the polarization when light is passing through. This allows to reduce or eliminate reflections of reflected light depending on the position of the half wave plate. In an easy assembly the half wave plate 207 is located in front of the objective lens 201.

EXAMPLE 7

In the following a description of various alternative detector systems is provided.

Figure 24:
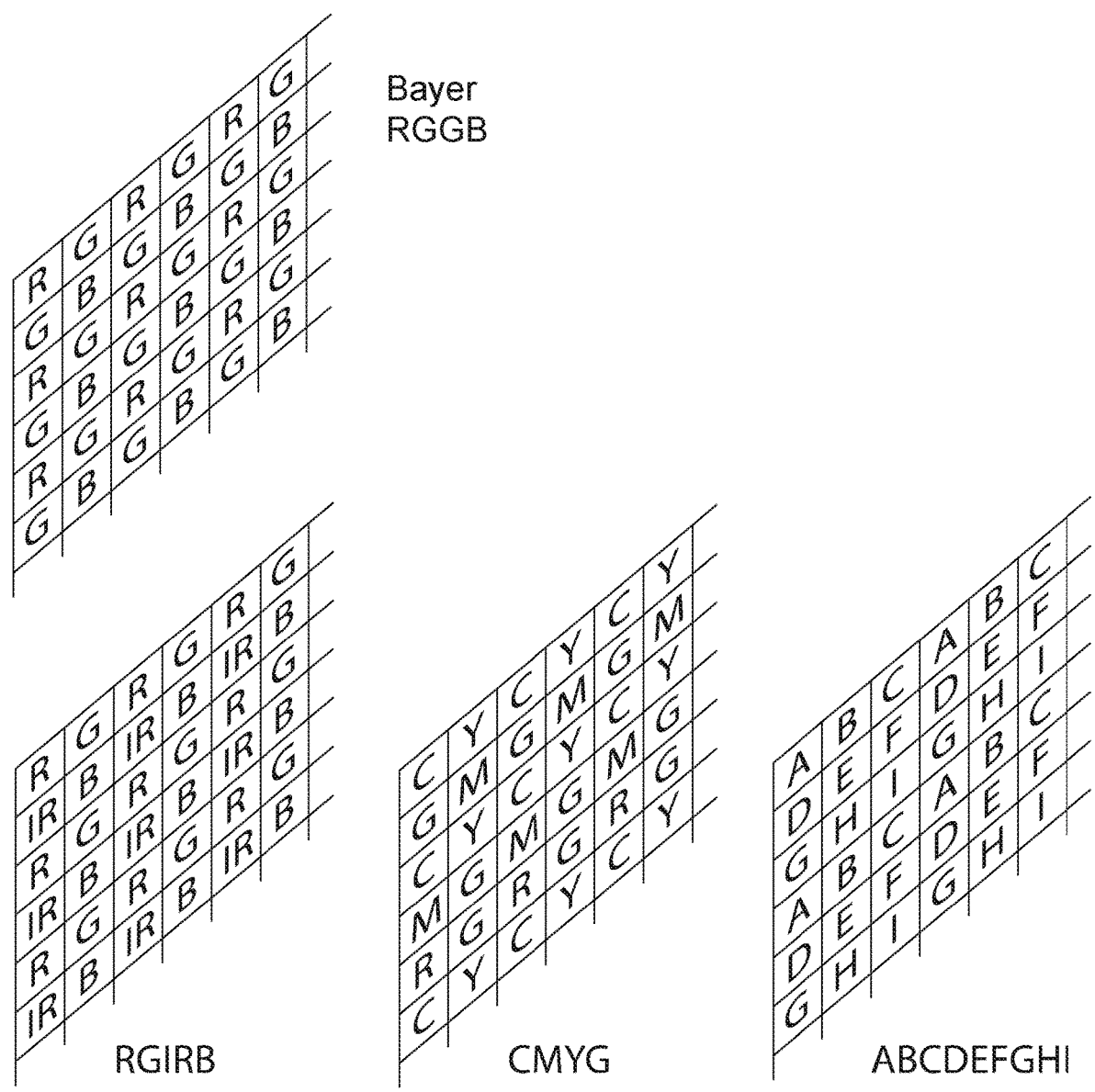
Figure 23:
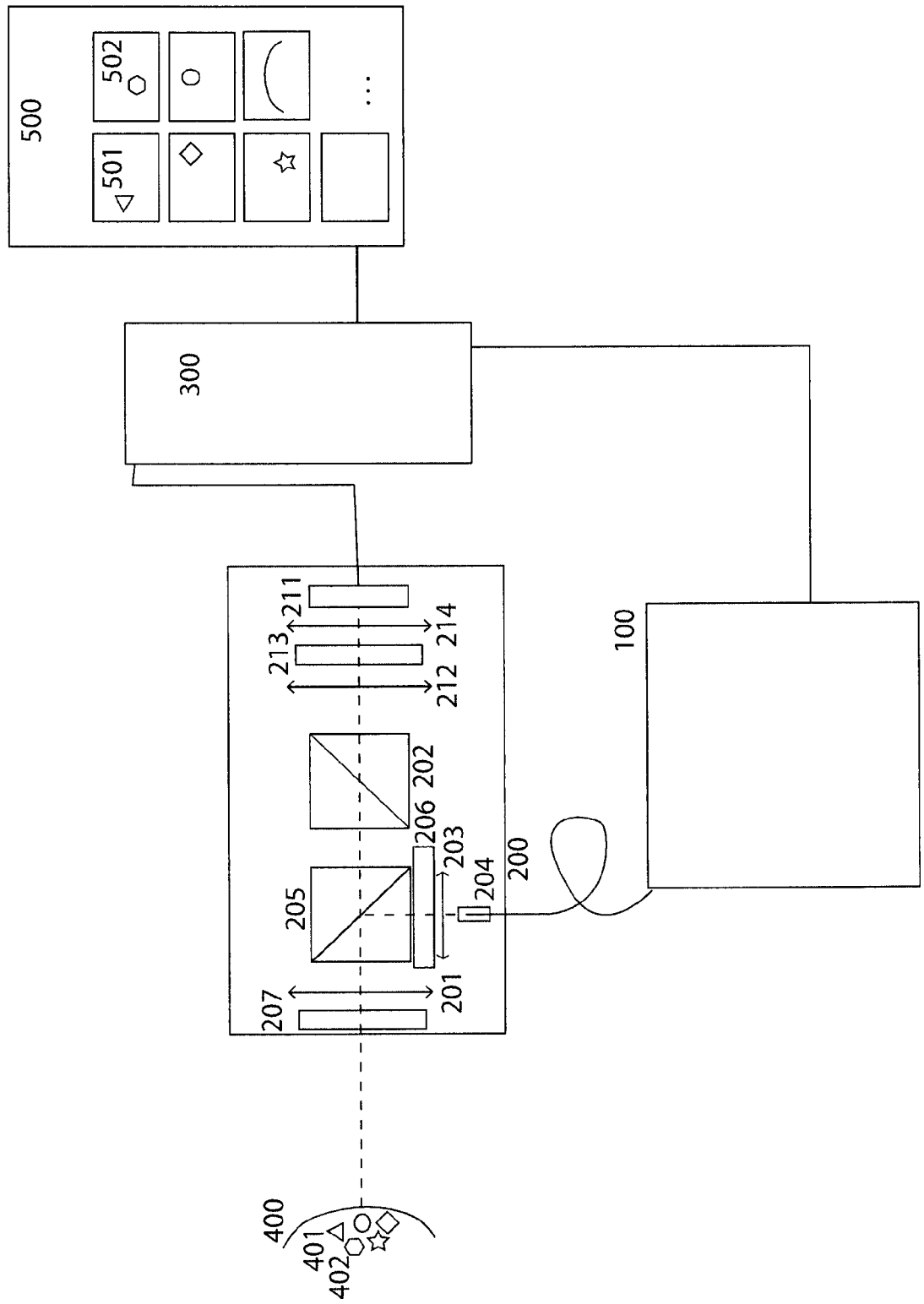

As a general description, the sensor 211 is a multichannel color sensor. This means that the sensor records the light field in multiple distinct spectral distributions. This can be achieved with various options: a) sensors that have microfilters in front of the pixels following the Bayer RGGB microfilter pattern or modifications of this like the RG(IR)B, the CMYG, b) any other filter mosaic patterns where each pixel records light with a distinct spectral distribution, and/or c) any further beam splitting, color filtering and imaging on monochrome sensors. Some of these patterns are shown in FIG. 24.

In general, the RGGB pattern achieves more accurate color reproduction, while the CMYG can be more sensitive. The full resolution color image can be retrieved by demosaicing, which can take place in the camera hardware, or later in image processing. The microfilter pattern can in general be extended to multiple colors or multiple spectral transmission profiles like ABCDEFGHI etc. An example like this is the lithographically patterned dichroic filter array as disclosed in U.S. Pat. No. 6,638,668 B2.

Figure 25:
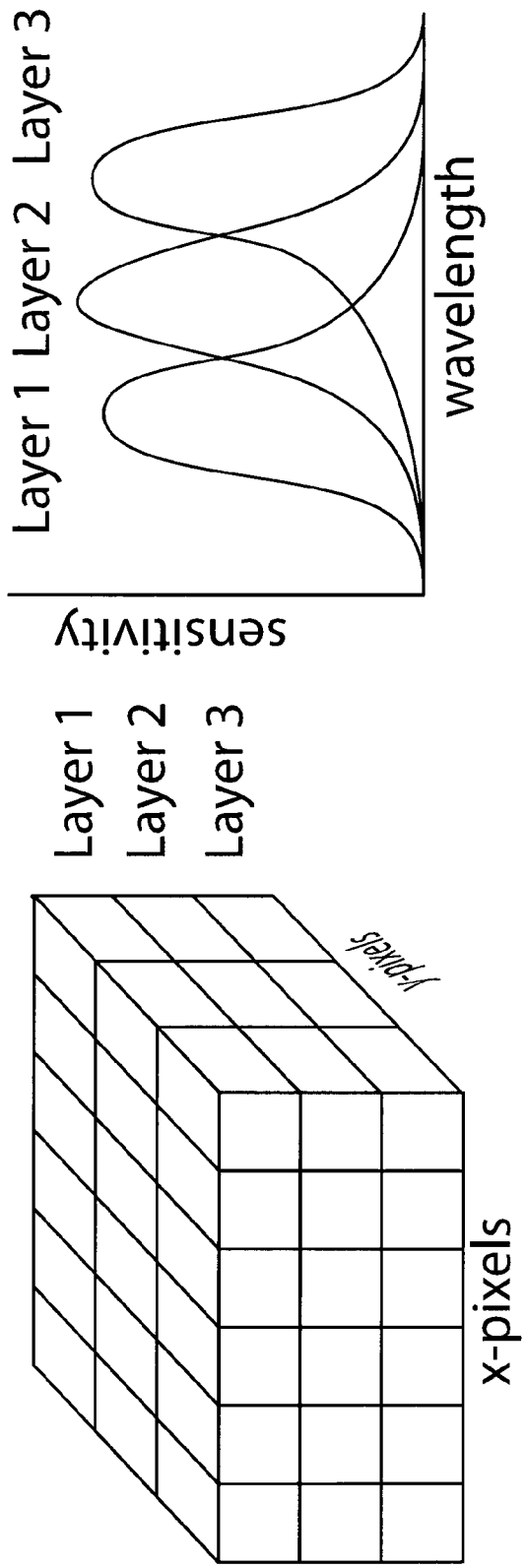
Figure 26:
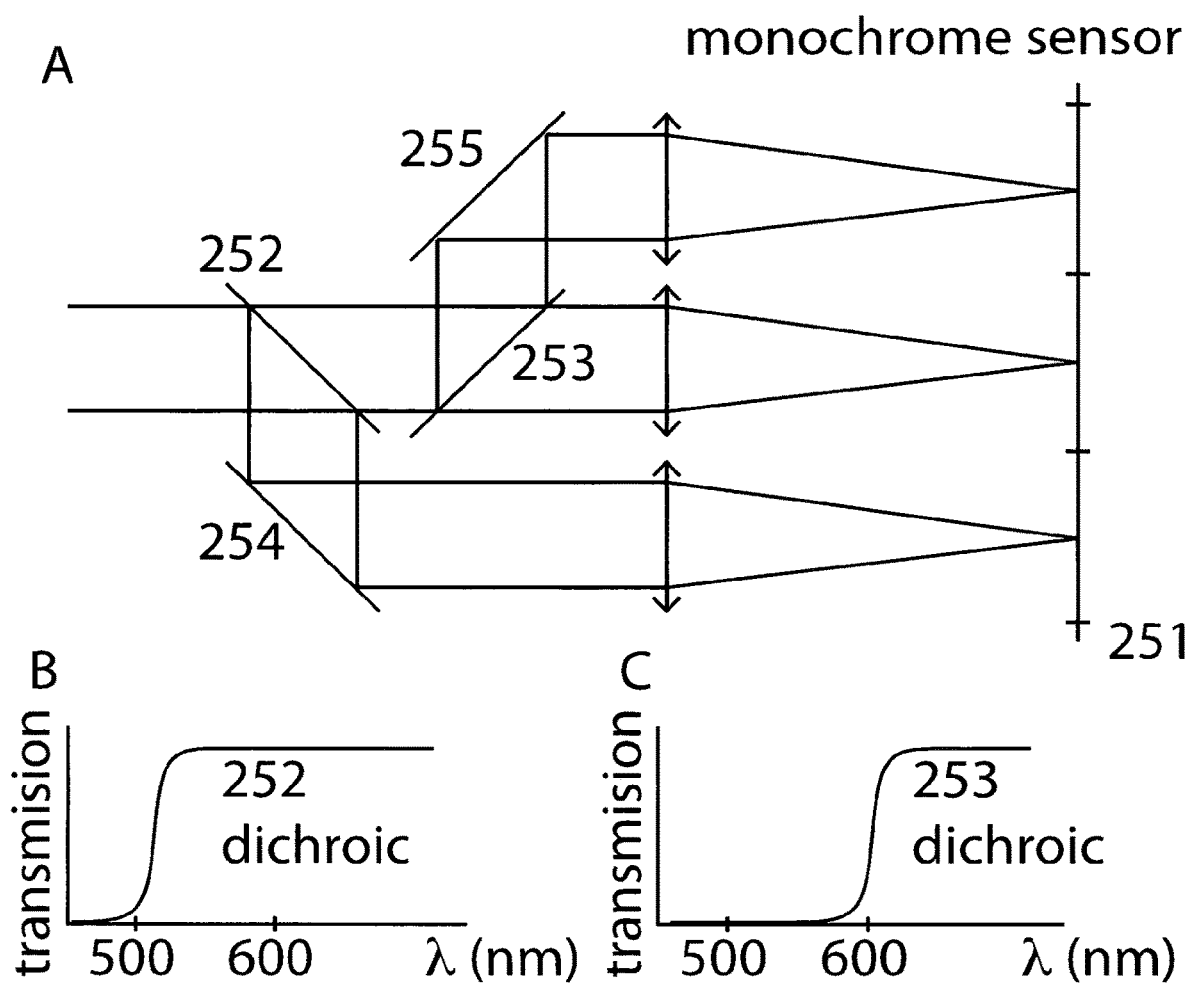

Alternatively, the multichannel color sensor can be based on Foveon X3 (see U.S. Pat. No. 6,632,701) sensor or similar technologies as shown in FIG. 25. In contrast to the microfilter patterns, the Foveon sensor is having photosensors spatially arranged in x- and y direction and that multiple layers (layer 1, layer 2, . . . ) are vertically stacked. Each layer is sensitive to different spectral areas due to the silicon absorption and the different transmission depths for the layer above light, thus the images generated of each layer corresponds to different color. With this it is possible to achieve higher spatial resolution.

In alternative embodiments shown in FIG. 26A the light beam to be detected is split in three parallel partial beams with the use of beam splitters/or mirrors 252, 253, 254, 255 and filtered with filters or with dichroic mirrors. Further the multichannel sensor 211 as shown in FIG. 3 is replaced by a monochrome sensor 251. Each filter or dichroic mirror has a particular transmission spectral profile, that transmits light of one out of three different colors as shown in FIGS. 26B and C. Thus different images are formed laterally distant to each other in the monochrome sensor each imaging a different spectral band.

Further, a multiple color channel can be implemented with multiple light splitting and filters, such as the prism 3-CCD geometry disclosed in U.S. Pat. No. 3,659,918. In this or similar light splitting implementations each path is filtered to carry light with the spectrum of the specific color, for example RGB. This approach can be extended to similar multiple beam splitters that offer multiple imaging paths (3 and more).

EXAMPLE 8

For most fluorescence applications ambient light needs to be avoided or blocked because its intensity is several orders of magnitude stronger than the intensity of the fluorescence light emerging from the fluorescent dye. Ambient light might come from the sun and pass through the windows onto the object or it might be emitted by the room lights. In current state-of-the-art systems, the environment is dark in order to avoid the intensive signal from ambient light in the fluorescence channels. As an alternative the specific wavelength regions of ambient light, which would pass the emission filter, may be blocked by filters. Unfortunately such filters are usually very expensive and it is not possible to cover big windows or room lights with such filters or they are just not available for any spectral configuration.

The technology presented here describes an alternative idea allowing ambient illumination of the room and at the same situation to detect fluorescence. This improvement has particular importance in surgical fluorescence imaging during open surgery.

Two different options are presented. Both options operate with pulsed light sources as ambient illumination. In the first method/embodiment all the light in the imaging path is blocked during recording (referred in the claims as "holding the recording") of a frame, and the second method/embodiment uses the dead times of the sensor array in between frames for ambient illumination.

EXAMPLE 8 A

Figure 27:
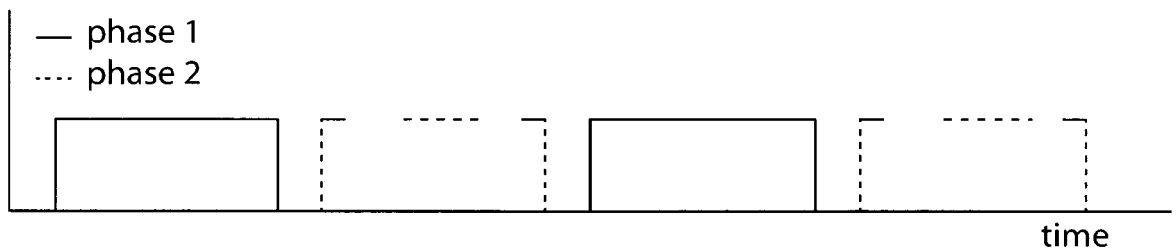
Figure 27:
Figure 27:
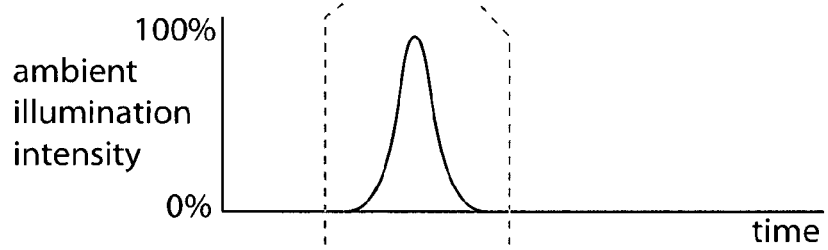
Figure 27:
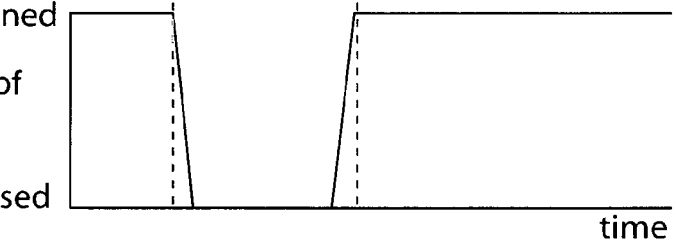

The illumination of the room lights are pulsed at a high frequency compared to maximum frequency perception of the human eye (for example at 200 Hz). The duration (duty cycle) of the pulses is typically a small fraction of the whole period (for example 5-20% of the period, typically 0.1-5 ms) which allows longer exposure time for the fluorescence imaging as shown in FIG. 27. The light path for imaging fluorescence signals is blocked during the pulses of light of the ambient illumination. The figure shows the phases of the imaging system and the respective timing of the shutter device to allow ambient illumination.

Figure 28:
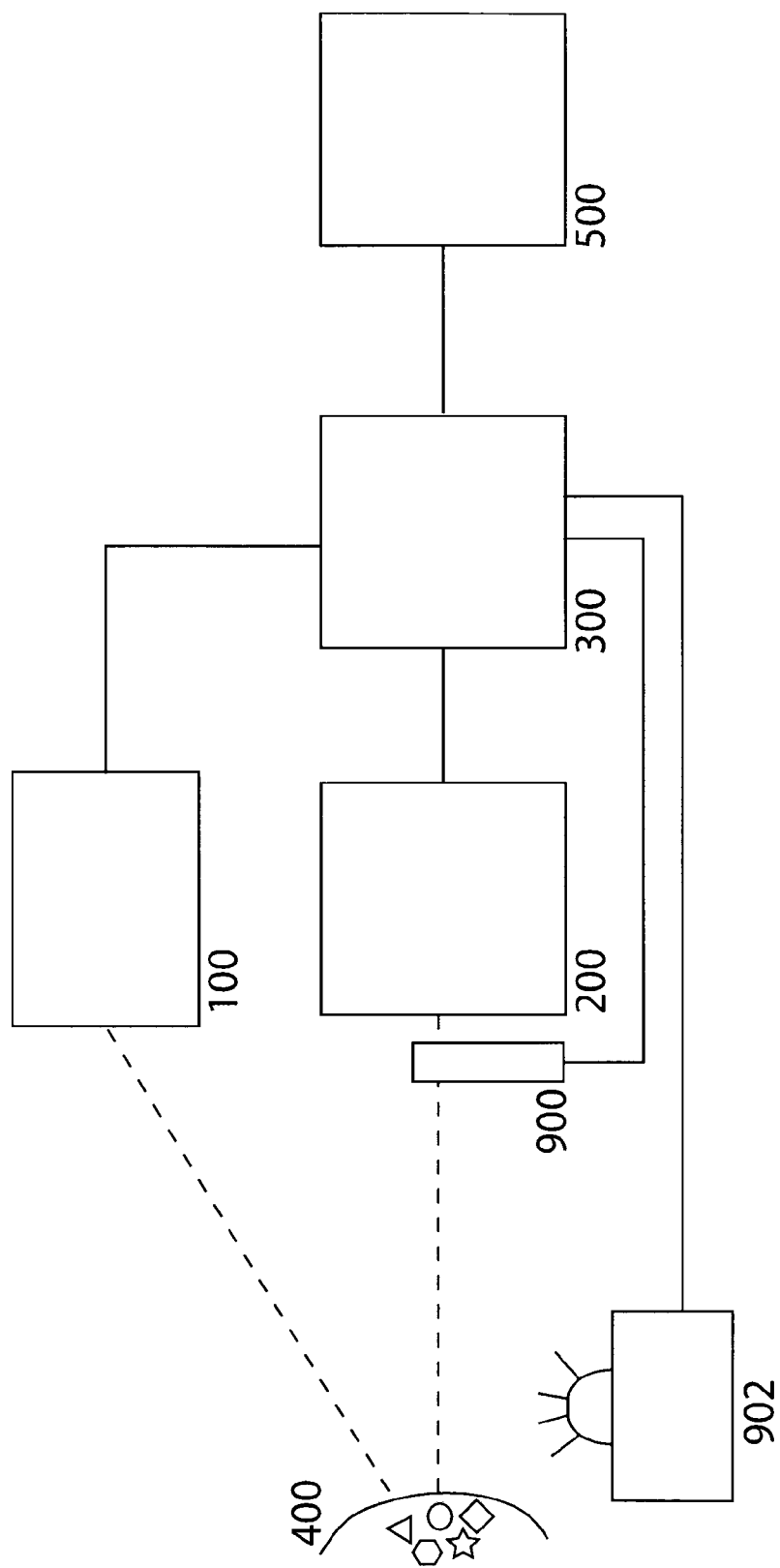

In an embodiment shown in FIG. 28 a room illumination/ambient illumination light source 902 is provided, the light of which is coupled into the excitation light path. Further an additional shutter 900 is provided in the imaging path. In this embodiment the shutter is placed in front of the objective lens of the optical system 200 for simplicity reasons. Nevertheless it can also be placed at another position in the path. Alternatively, the shutter device 900 can be included in the imaging path directly in front of the sensor arrays. Both, the shutter 900 and the room illumination 902 are controlled from the control/processing unit 300.

When the shutter 900 is closed, it blocks all the light from entering the imaging/detection path and therefore light does not reach the sensor array in the sensor system 200. The frequency of operation of the ambient illumination from source 902 is not necessarily adapted to the frequency of operation of the fluorescence imaging system. It is preferable if the imaging system runs at 30-60 Hz to generate a fluent stream of images of fluorescence and reflectance for the human eye. The ambient illumination 902 is preferably operated with a frequency which is higher so the human eye does not perceive any flickering in the room environment.

Preferably, the frequency of operation of the ambient lighting system 902 is a higher harmonic of the frequence of the imaging. In this case each sequentially taken picture is equally influenced by the closed imaging path. But it would also be possible to detect the ambient illumination timing and digitally correct the imaging data for the influence of the slightly differently shuttered imaging path if necessary.

Figure 29:
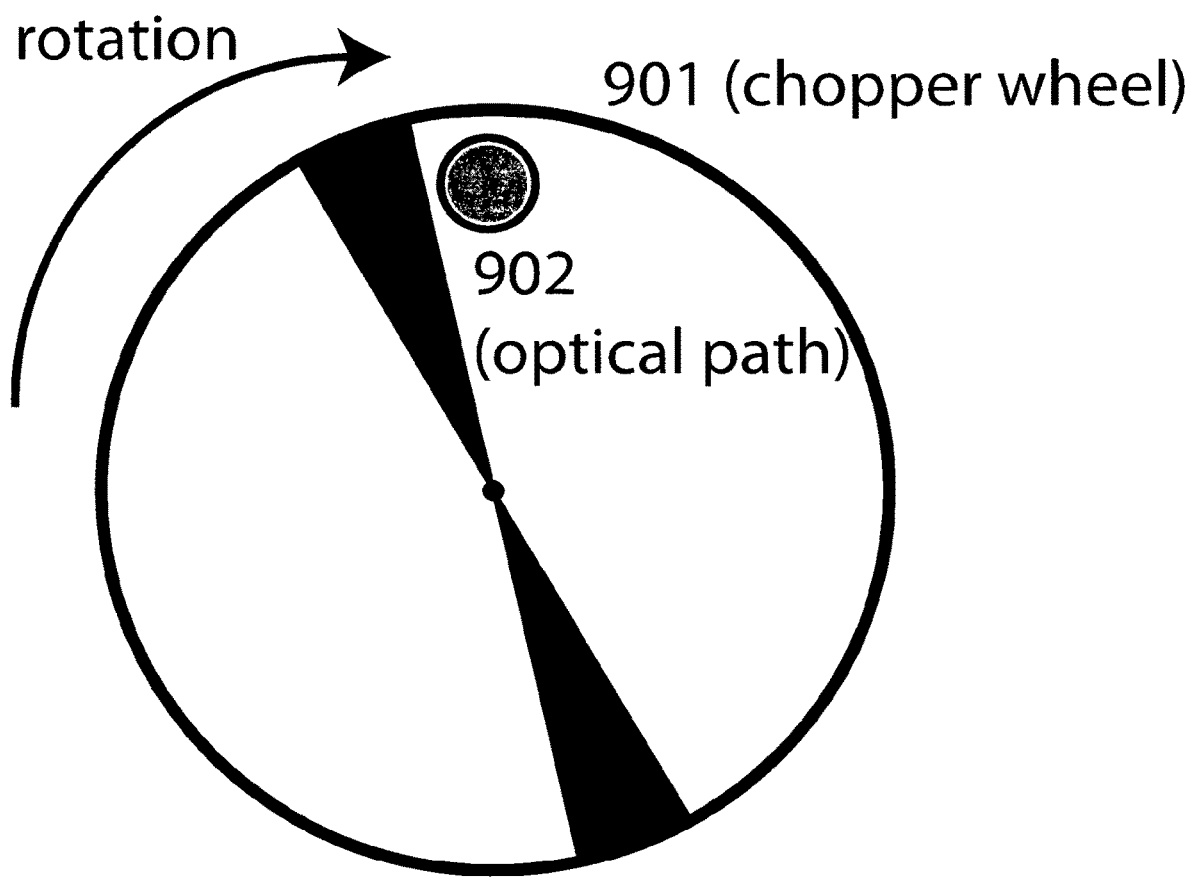

The shutter 900 can be any electromechanical device that can allow or block light from propagation along the beam path. In a preferred embodiment the ambient light and the optical imaging path 903 is shuttered by a beam chopper wheel 901 as shown in FIG. 29 rotating at half the frequency of the shutter effect.

Chopper wheels 901 are a good choice to interrupt imaging paths with a certain frequency and usually operate at higher frequencies compared to optical shutters. Alternatively, a chopper wheel can be exchanged by different devices like electro optical modulator, SLMs, or acousto-optical modulators to hold the recording of the image by making the path opaque. In another alternative, the path is closed using polarization filters and using electronic devices with a variable polarization sensitive transmission of light. This also allows to effectively block the imaging path.

The light source can be any type of ambient light source that can operate with short pulses. The light source 902 preferably consists of electronically pulsed LEDs. Such LEDs are well suitable for the ambient illumination of an operation theater and can be pulsed very precisely and at a very high frequency compared to the frequency of the human eye.

EXAMPLE 8 B

Figure 30:
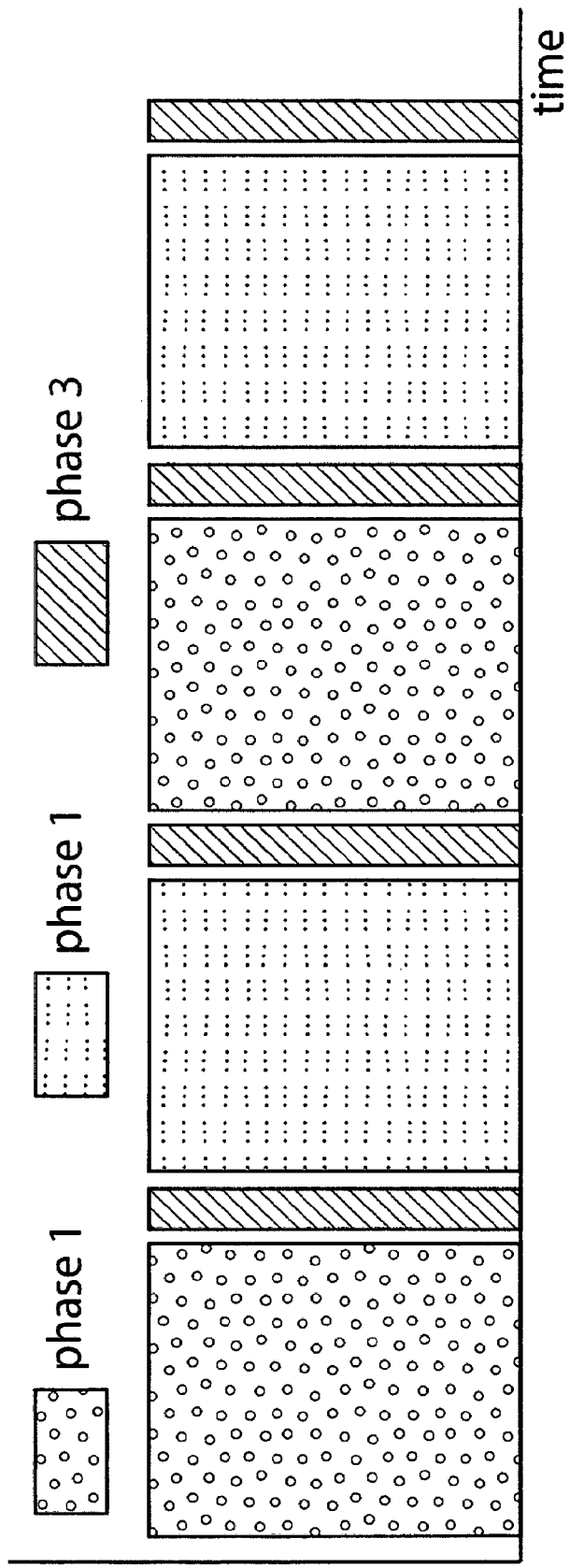

An alternative embodiment as shown in FIG. 30 uses an additional phase (3rd phase) of illuminating light from a different light source always between the phases 1 and 2 of the imaging setup for ambient illumination. This phase runs at double the frequency of the other phases. The light source can either be independent similar to the light source 902 or be included in the light source 100 of the illumination system. The light emitted by this light source is not necessarily used for imaging, but may mainly be used to improve the visual perception for the human eye in the object and/or the surrounding environment.

In the basic embodiment the illumination of the imaging area is optimized only for the detection of image components and the image processing, and in particular for the unmixing of the different fluorophores. Typically, such an illumination is not optimal for the visual impression for a surgeon and may result in a low image contrast and non-natural visual impression. The spectral distribution and intensity of the additional third illumination phase however is free to optimize the overall visual perception and brightness for the user (surgeon and medical personnel in the OR) as perceived accumulatively for all illumination phases.

The illumination pulses in the 3rd phase are short enough to fit in the dead time of the imaging sensors between the two phases as shown in FIG. 30. Usually dead times occur when transferring data from the sensor 200 to the controlling unit 300. Thus short pulses of ambient light with high accuracy are required. If the imaging system works at a frequency of 30 Hz, the pulsed ambient illumination may work at double of this frequency, i.e. 60 Hz. If the ambient illumination should just consume a duty cycle of 1%, the pulse width of the pulses should be in the order of 170 µs. If the ambient illumination consumes 5% duty cycle, the additional illumination phase provides a brighter field, and the pulsed ambient illumination duration is 800 µs.

EXAMPLE 9

In the preceding descriptions, the concept of a combined spectral and time multiplexing system is described using illumination of an object with two different phases. Nevertheless, the invention may be extended to further phases in more elaborate imaging scenarios. These allow for example to acquire additional spectral information on the reflection and/or the fluorescence images. In the following section, additional examples of multiple phase systems will be described in detail.

EXAMPLE 9A

Figure 31:
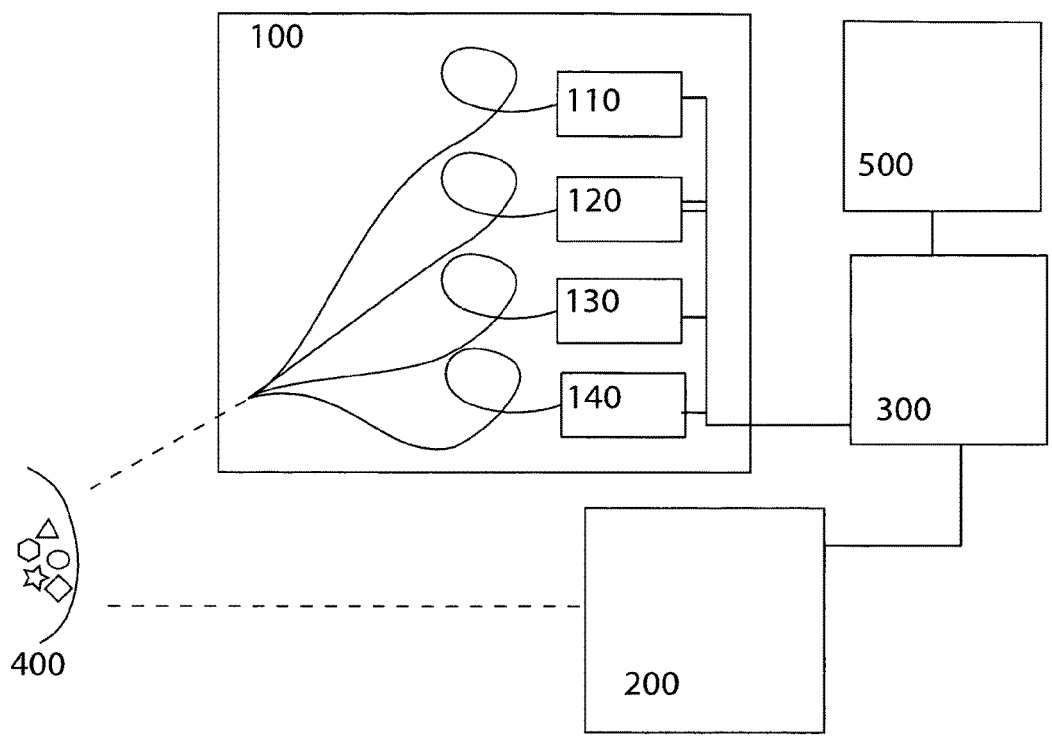
Figure 32:
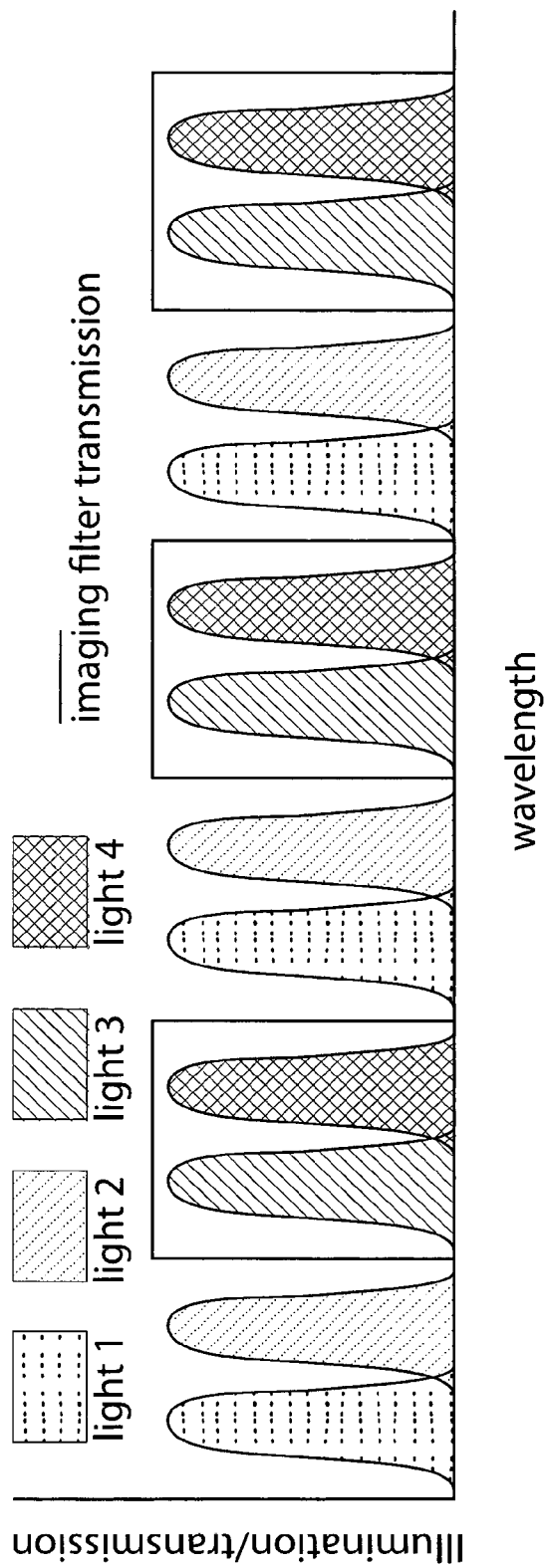
Figure 33:
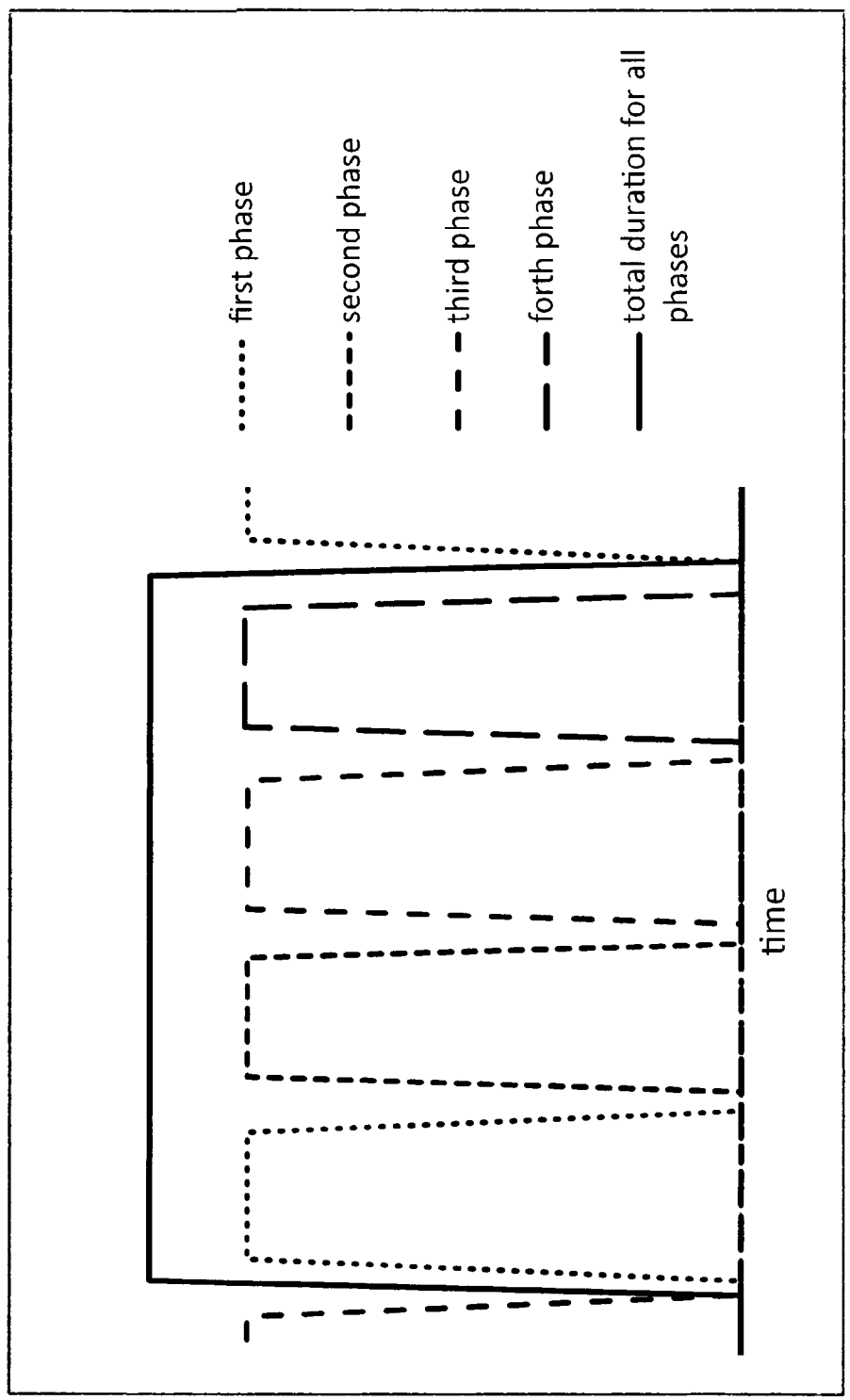
Figure 34:
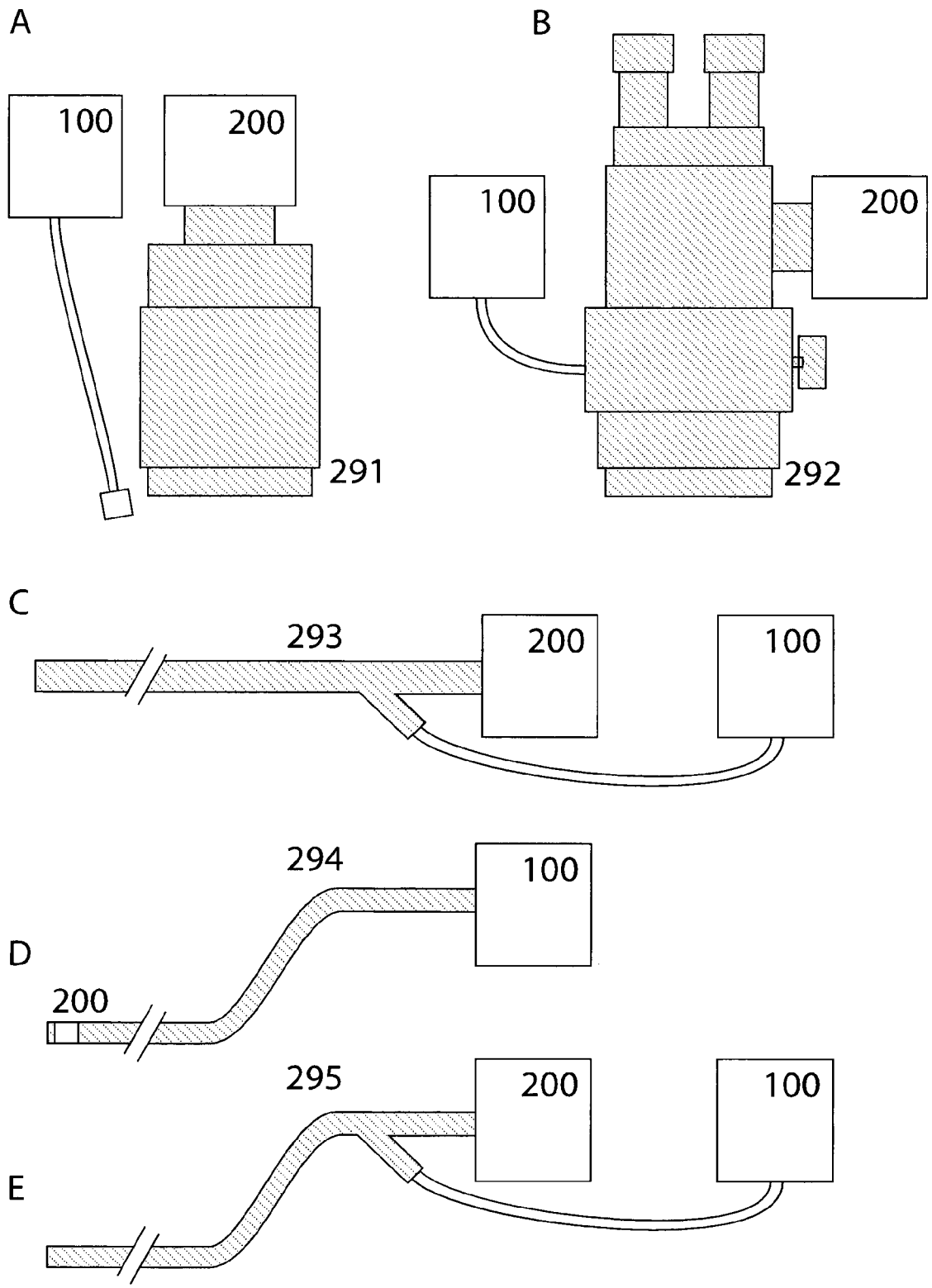

In FIG. 31 a method operating in 4 phases with 4 light sources is described. This example has four different light sources 110, 120, 130 and, 140 and an imaging system 200 that transmits the light in multiple bands. The respective example emission spectra of the light sources as well as the light transmission in the imaging (detection) system 200 are shown in the FIG. 32. The spectral profile of all four lights consists of multiple spectral bands. The spectral bands of light 1 and 2 are coinciding with the spectral attenuation bands of the imaging system, while the spectral bands of lights 3 and 4 are coinciding with the transmission bands of the imaging system. As shown in FIG. 33 (time course of illumination) the sample is illuminated sequentially in 4 phases by the four light sources 110, 120, 130 and 140. In each phase one light illuminates the object 400. In this particular example light 1 and light 2 excite the fluorescence subsequently. The filter in the imaging system attenuates the reflected excitation lights, while transmitting the fluorescence emission, and fluorescence emission images from illumination with the first light and the second light are formed. Subsequently the object 400 is illuminated with lights 3 and 4. Lights 3 and 4 are reflected by the object and are transmitted through the imaging system to form the reflected light. In total 4 images are recorded, each originating from each illumination phase. The two fluorescence images (when illuminating with lights 1 and 2) are combined by the processing unit 300 to form a composite fluorescence image that is processed to spectrally unmix the fluorescence components, and the two reflectance images (when illuminating with lights 3 and 4) are combined by the processing unit 300 to form a composite reflectance image that is processed to spectrally unmix the reflectance components.

Assuming that each sensor has 3 detection channels (for example a standard RGB camera), after the completion of 4 phases, the system records combined reflectance images from 6 channels and combined fluorescence information from 6 channels.

There are various alternatives of the multiphase spectral multiplexing method. The spectral profile of each light does not need to be spectrally separated from the adjacent ones, but there can spectrally partially overlap, but not being the same. The only condition necessary is that the lights designated to excite fluorescence should not have a spectral component within the transmission band of the imaging system 200. Additionally, they don't have to be operated sequentially, any order is possible. Another alternative may have different combinations of lights for excitation. For example when using one light for fluorescence and three for reflectance with an RGB sensor it is possible to combine the fluorescence images and decompose them to 3 fluorescence components and 9 reflectance components. Or when using two lights for fluorescence and one for reflectance, it is possible to combine the images and decompose it to 6 fluorescence components and 3 reflectance components

EXAMPLES 10

The multispectral imaging method and system can be implemented by integrating into various imaging instruments. In a first embodiment shown in FIG. 34A a multispectral imaging system is used with a zoom lens 291 as an objective lens by attaching the detector 200 with a camera adaptor. The illumination system 100 delivers the light to the object with a light guide.

In another embodiment shown in FIG. 34B the detection system 200 is connected to the video port of a surgical microscope 292 and the illumination system 100 is connected with a light guide to the illumination port to illuminate the object through the objective lens of the microscope.

In a further embodiment shown in FIG. 34C, the detection system 200 is connected to the eyepiece port of a rigid endoscope optionally with the use of an adaptor and the illumination system 100 is connected with a light guide to the illumination port.

In a further embodiment shown in FIG. 34D the detection system 200 is miniaturized and integrated into the tip of a flexible endoscope, while the illumination system 100 is attached to the illumination port of the endoscope.

In yet another embodiment shown in FIG. 34E, the detection system 200 is connected to the camera port of a flexible fiberscope, which transfers the image from its tip to its distal point with the use of a flexible fiber bundle, and the illumination system 100 is connected to the illumination port.

EXAMPLE 11

Figure 35:
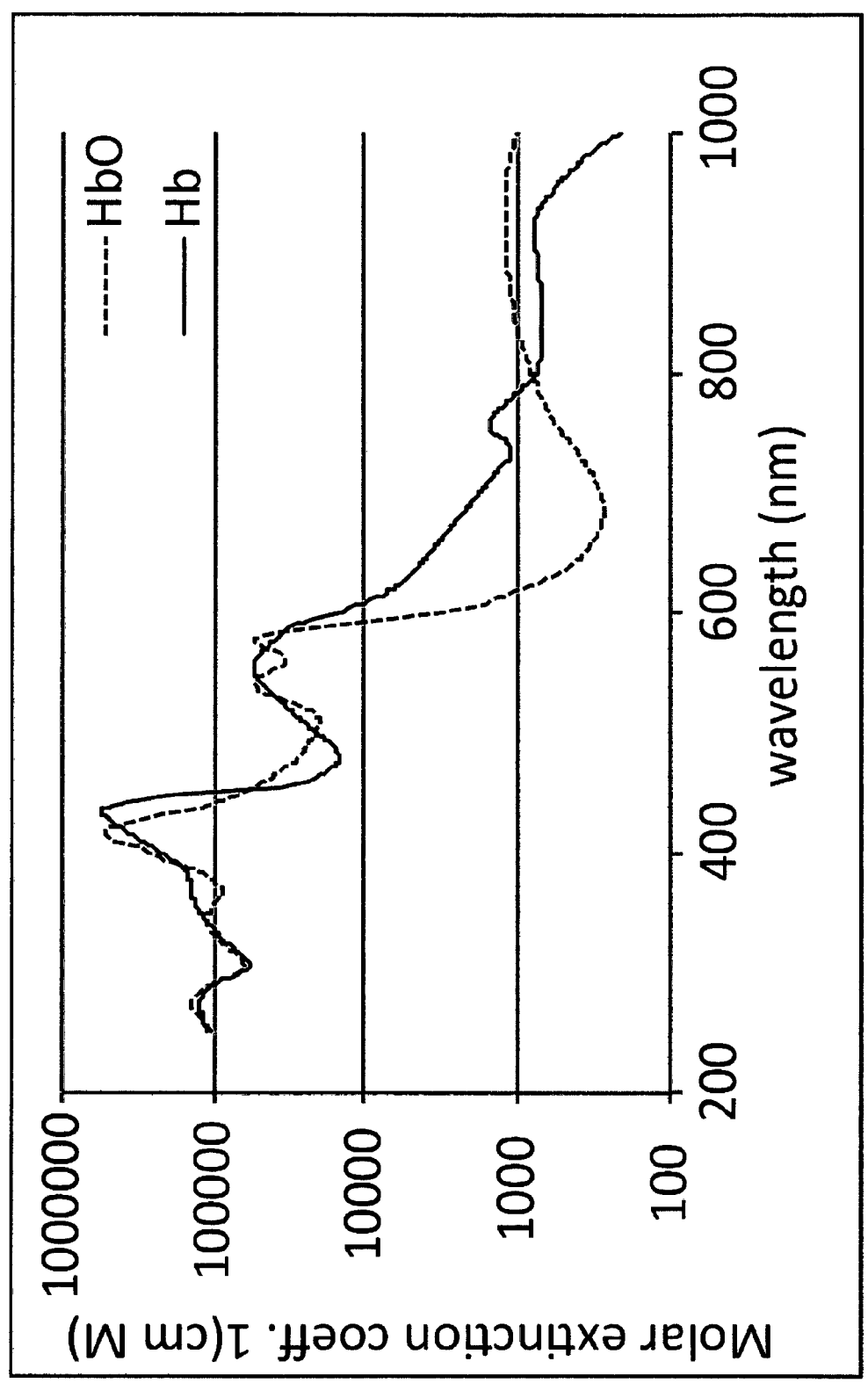

In the following several possible applications of the present inventive method are described.
a) Application Scenario: Imaging of Blood Oxygenation:

In the following example oxygen saturation is imaged by assessing the relative concentration of oxygenated to de-oxygenated hemoglobin (HbO and Hb) on tissue. Since HbO and Hb have distinct absorption spectra as shown in FIG. 35, the reflected light carries spectral profile information that can be recorded in the system. By spectrally unmixing the multiple reflectance components it is possible to generate a) an RGB image to be displayed in a visualization system b) an additional map of the biodistribution of the HbO and Hb components. The oxygen saturation maps are calculated by the ratio between the HbO to the total hemoglobin saturation.
b) Application Scenario: Detection of Cancer Lesions, Anatomical Features, or Functional Conditions Another envisioned application is to use the system to visualize the biodistribution of injectable fluorescent contrast agents for in-vivo clinical diagnostic imaging. These fluorescent contrast agents may be non-targeted, like Fluorescin or Indocyanin Green to highlight vascularization, blood perfusion etc., or targeted in a way that can highlight with fluorescence diseases, such as cancer, medical conditions, such as inflammation, or anatomical features, such as neures or lymph nodes, by binding to molecular sites associated to relative functional or pathological activity in tissue. An example is the imaging of glioblastoma tumors during brain surgery, using 5-ALA, a compound that induces the production of protoporphyrin in cancer cells. These applications may involve the integration of the invented method in medical imaging systems like surgical microscopes, endoscopes, laparoscopes, gastroscopes, bronchoscopes, ophthalmoscopes, fundus cameras, etc.

c) Application Scenario: Multi Reporter Imaging

Of particular interest is the application of the invented real time multispectral imaging technology in clinical applications utilizing dual reporter diagnostic approaches. The use of two or more fluorescent probes can provide diverse information on different biomarkers to access the pathological or functional condition of tissue. The combination of the biodistributions of different agents, that they come as image components after unmixing can enhance the visualization of a target to be imaged, i.e. a lesion, increase the detection sensitivity and specificity of a pathological feature.

d) Application Scenario: Machine Inspection

An additional envisioned application scenario of real time multispectral fluorescence imaging is on machine inspection. An engine or mechanical parts that are difficult to visually inspect, such as gears, because they are internally enclosed, may have damages like small cracks. These structural defects can be visualized after flushing the inside of the engine with a fluorescent solution and using an endoscope to inspect internally the location of cracks that retain the fluorescent fluid. Real time multispectral imaging can offer simultaneous color reflectance and fluorescence images.

e) Application Scenario: pH Sensitive Dyes

The chemical environment can influence the emission or the excitation of fluorescent dyes. One of these parameters changing the dye absorption and emission characteristics is the pH value.

Case of Emission Sensitive Dyes:

It is preferable to have the transmission bands of the respective filters optimized in a way to detect signal which is spectrally sensitive to changes of the pH value. It is also preferable to have detection channels, which depend maximally on the pH value, whereas others are mostly insensitive to changes in pH value.

This can be realized for example by adjusting the emission filter bands such that the center of the respective measured fluorescence bands either match a spectral point where the dye emission spectrum varies maximal on a change of pH value or on a spectral point where the dye emission spectrum minimally depends on the pH value.

Case of Excitation Sensitive Dyes:

It is preferable to have the excitation bands of the respective filters and light sources optimized in a way to detect signal which is spectrally sensitive to changes of the pH value. It is also preferable to have excitation bands so that some of the detected channel(s) depend maximally on the pH value, whereas other channel(s) are mostly insensitive to changes of the pH value.

The excitation filter bands should be adjusted such that the center of the respective bands either matches a spectral point where the dye excitation spectrum varies maximal on a change of pH value or on a spectral point where the dye excitation spectrum minimally depends on the pH value.

The recorded images are multi spectrally recorded, spectrally unmixed and processed in such a way that they visualize the spatial distribution of the pH values.

f) Application Scenario: Distinguishing Tumor Infiltration Zone and Solid Tumor Mass by Differences in the PPIX Emission Spectrum For tumor diagnostics, 5-ALA is administered to the patient leading to an accumulation of protoporphyrin IX (PPIX) in tumor tissue. The substance PPIX is both, a fluorescent dye and also an agent for photodynamic therapy.

The fluorescence emission spectrum of the PPIX varies depending on the location and the microenvironment inside the tumor. More precisely the infiltration zone exhibits a different fluorescence emission spectrum compared to the solid tumor mass. This spectral difference can be used in order to differentiate between the tumor mass and the infiltration zone.

Two different peaked PPIX spectra with maxima at 620 nm and 635 nm can be recorded and unmixed with the inventive system.

Additionally, other fluorophores and also autofluorescence can be recorded.

g) Application Scenario: Autofluorescence

An interesting application is the spectral detection of the intrinsic tissue autofluorescence, that is the fluorescence usually emitted without administering fluorescent contrast agents e. g. fluorophores). The tissue intrinsic autofluorescence is attributed to various molecules that exist or are produced in the tissues, such as NADPH, flavins, collagen, elastin, and others. The existence, production, accumulation, or other concentration properties is linked to various tissue features, such as anatomical, functional, and pathological features. The multispectral imaging of tissue autofluorescence and the spectral unmixing of the associated compounds according to the invention can reveal features or characteristics of tissue that aid the assessment or the diagnosis of a medical condition. Multispectral imaging and unmixing of the autofluorescence can take place together with systemically administered fluorescent molecules.

h) Application Scenario: Retina Imaging

The retina can be imaged through the eye. Currently this imaging modality is used in clinical practice mainly for diagnostic purposes of the retina itself.

The eye provides a clear window to the blood vessels of the body looking directly in the retinal vessels. With multispectral imaging of the retina and spectral unmixing according to the invention it is possible to identify fluorescent molecules that are either existing in the retina or circulate in its blood vessels. These fluorescent molecules may have been systemically administered, to freely circulate or to target cells (possibly metastatic cancer cells), microorganisms, viruses, or molecules. Multispectral imaging and unmixing can identify these substances, which can provide information about the blood circulation in general, or the circulation of the targets, that can help to assess the functional, or pathological condition of the "patient". Therefore it is possible to use retina imaging to obtain information about the retina itself and also to obtain information about compounds circulating in the blood.

i) Application Scenario: Robotic Surgery

An interesting application of the multispectral imaging and system is to combine it with a surgical robotic system. At a first place, it can provide the surgeon that operates with visual multispectral information either in the reflectance color domain, or in the (auto-)fluorescence domain, about tissue anatomy, function or disease. At a second level can provide input that increases the safety of the robot operation, for example prohibiting the doctor from accidentally damaging (i.e. cutting) tissue (for example, nerves). At a third level it can directly provide input and or feedback to an automated robotic surgery procedure that has reduced or minimum human controlling.

The invention claimed is:

1. A method for acquisition of fluorescence and reflectance images of an object comprising the steps of
   alternatingly illuminating the object with at least a first light having at least two spectral regions of high intensity, wherein the first light has regions of low intensity that are of longer wavelengths to a region of high intensity, and at least a second light having at least one spectral region of high intensity,
   wherein the ratio of the light intensity between regions of high intensity at shorter wavelength and regions of low light intensity of longer wavelength for the first light is $\geq 1 \times 10^2$,
   recording a first image of the object during illumination of the object with the first light and a second image of the object during illumination of the object with the second light using a common sensor array,
   wherein the light recorded by the sensor array is attenuated in at least said two of the spectral regions in which the first light has high intensities,
   wherein the sensor array is a multichannel array where each channel has a distinct spectral sensitivity,
   wherein the light recorded by the sensor array is attenuated by a multiple-bandpass filter with transmission characteristics, which are complementary to the first light, so as to attenuate at least said two spectral regions in which the first light has high intensities, and
   wherein at least one of
   (a) the attenuation ratio between the intensity of the unattenuated to the attenuated spectral regions is $\geq 1 \times 10^2$, and
   (b) the amount of attenuation of the light recorded by the sensor array in at least one of the spectral regions in which the first light has high intensities is such that the intensity of the light recorded in unattenuated spectral regions is higher than the intensity of the light recorded in the sum of the attenuated spectral regions.

2. The method according to claim 1, wherein the multichannel array is a color sensor array.

3. The method according to claim 1, wherein the data, which are provided in the channel image space of the recorded images, are transformed into values of a component image space.

4. The method according to claim 3, wherein the components correspond to spatial distributions of fluorochromes, absorbers, derived values, or noise.

5. The method according to claim 1, wherein the ratio of the light intensity between at least one region of high intensity at shorter wavelength and at least one region of low light intensity of longer wavelength for at least one of the lights is $>1 \times 10^3$.

6. The method according to claim 1, wherein the first light, the second light, or both the first light and the second light is/are generated by at least one of
   (a) by white light, from two broadband light sources, wherein said broadband lights are filtered by multiple bandpass filters in order to generate the first light and the second light,
   (b) multiple narrowband light emitting diodes (LED), where the light emanating from the narrowband light source or light emitting diodes is filtered by a multiband filter in the light path, and
   (c) a combination of broadband light sources according to (a) and narrowband light sources according to (b).

7. The method according to claim 1, wherein the image recorded during illumination of the object with the second light is processed in order to correct the image for the attenuated spectral regions.

8. The method according to claim 1, wherein the object is illuminated with second light for generation of first reflected light reflected by the object and with two or more spectrally different first lights for excitation of two or more, spectrally different, fluorescence lights emitted by the object, alternating between the second light and each of the two or more first lights, and
   recording first images of the object during illumination of the object with each of the first lights and a second image of the object during illumination of the object with the second light using a common sensor array,
   wherein the light recorded by the sensor array is permanently attenuated in one, several or all the spectral regions of all first lights, in which the first lights have high intensity to an amount that the intensity of the light recorded in unattenuated spectral regions is higher than the intensity of the light recorded in the attenuated spectral regions.

9. The method according to claim 1, wherein
   alternatingly illuminating the object with at least the first light, having a first illumination period, and the second light, having a second illumination period, and
   illuminating the object with pulses of a further light, wherein the pulse duration of the further light is short compared to the first illumination period and short compared to the second illumination period, and holding the recording of the first image and the second image during said illumination with further light,
   or
   alternatingly illuminating the object with at least the first light, having a first illumination period, the second light, having a second illumination period, and a third light having a third illumination period.

10. An imaging apparatus for acquisition of fluorescence and reflectance images of an object comprising
    at least a first light source providing a first light having at least two spectral regions of high intensity and at least a second light source providing a second light having at least one spectral region of high intensity, wherein the first light has at least regions of low intensity that are of longer wavelengths to a region of high intensity,
    wherein the ratio of the light intensity between regions of high intensity at shorter wavelength and regions of low light intensity of longer wavelength for the first light is $\geq 1 \times 10^2$,
    wherein the at least one first light source and the at least one second light source are configured to alternatingly illuminate the object with the first light and the second light,
    a sensor array arranged for recording a first image of the object during illumination of the object with the first light and a second image of the object during illumination of the object with the second light,
    wherein the sensor array is a multichannel array where each channel has a distinct spectral sensitivity, and
    an attenuator,
    wherein the attenuator comprises a multiple bandpass filter positioned between the object and the sensor array and having transmission characteristics, which are complementary to the first light, so as to attenuate the light recorded by the sensor array in at least said two spectral regions in which the first light has high intensities, and wherein at least one of
(a) the attenuation ratio between the intensity of the unattenuated to the attenuated spectral regions is $\geq 1\times 10^2$, and
(b) the amount of attenuation of the light recorded by the sensor array in at least one of the spectral regions in which the first light has high intensities is such that the intensity of the light recorded in unattenuated spectral regions is higher than the intensity of the light recorded in the sum of the attenuated spectral regions.

11. An apparatus according to claim 10, wherein the sensor array is a color sensor array.

12. The apparatus according to claim 10 configured to transform the data, which are provided in the channel image space of the recorded images, into values of a component image space.

13. The apparatus according to claim 12, wherein the components correspond to spatial distributions of fluorochromes, absorbers, derived values, or noise.

14. The apparatus according to claim 10, wherein the ratio of the light intensity between at least one region of high intensity at shorter wavelength and at least one region of low light intensity of longer wavelength for at least one of the lights is $>1\times 10^3$.

15. The apparatus according to claim 10, wherein the image recorded during illumination of the object with second light is processed in order to correct the image for the attenuated spectral regions.

16. An endoscope or a surgical microscope comprising an imaging apparatus according to claim 10.

17. A use of a method, apparatus, endoscope or surgical microscope according to claim 10 for recording reflection images or fluorescence images for at least one of (a) internal inspection in automotive applications, (b) in medical diagnostics, (c) in medical treatment, (d) in chemical analysis and (e) in physical analysis.

* * * * *